(12) United States Patent
McCann

(10) Patent No.: US 11,129,912 B1
(45) Date of Patent: Sep. 28, 2021

(54) RADIOPHARMACEUTICAL AND METHODS

(71) Applicant: Point Biopharma, Inc., Toronto (CA)

(72) Inventor: Joe McCann, Toronto (CA)

(73) Assignee: POINT Biopharma Inc., Indianapolis, IN (US)

( * ) Notice: Subject to any disclaimer, the term of this patent is extended or adjusted under 35 U.S.C. 154(b) by 0 days.

(21) Appl. No.: 17/162,856

(22) Filed: Jan. 29, 2021

Related U.S. Application Data

(60) Provisional application No. 63/051,335, filed on Jul. 13, 2020.

(51) Int. Cl.
| | | |
|---|---|---|
| *A61K 51/04* | (2006.01) | |
| *A61P 35/00* | (2006.01) | |
| *C07B 59/00* | (2006.01) | |

(52) U.S. Cl.
CPC .......... *A61K 51/0482* (2013.01); *A61P 35/00* (2018.01); *C07B 59/002* (2013.01)

(58) Field of Classification Search
CPC ................ A61K 51/04; A61P 35/00
See application file for complete search history.

(56) References Cited

U.S. PATENT DOCUMENTS

| | | | |
|---|---|---|---|
| 10,398,791 B2 | 9/2019 | Eder et al. | |
| 2007/0269375 A1* | 11/2007 | Chen .................... | A61K 51/088 424/1.69 |

FOREIGN PATENT DOCUMENTS

| | | |
|---|---|---|
| WO | 2015/171792 A1 | 11/2015 |
| WO | WO2018108237 * | 6/2018 |
| WO | 2020/061458 A1 | 3/2020 |

OTHER PUBLICATIONS

Martina Weineisen et al., 68Ga-and 177Lu-Labeled PSMA I&T: Optimization of a PSMA-Targeted Theranostic Concept and First Proof-of-Concept Human Studies, J Nucl Med, 56, 1169-1176. (Year: 2015).*
Kristell L.S. Chatalic et al., Towards Personalized Treatment of Prostate Cancer: PSMA I&T, a Promising Prostate-Specific Membrane Antigen-Targeted Theranostic Agent, Theranostics, 6(6), 849-861. (Year: 2016).*
Weineisen et al. EJNMMI Research 2014, 4:63.
Weineisen et al., "Materials and Methods", The Journal of Nuclear Medicine, vol. 56, No. 8 (Aug. 2015) 8 pages.

* cited by examiner

*Primary Examiner* — Michael G. Hartley
*Assistant Examiner* — Jagadishwar R Samala
(74) *Attorney, Agent, or Firm* — Mintz Levin Cohn Ferris Glovsky and Popeo, P.C.; Peter F. Corless; Joohee Lee

(57) ABSTRACT

The radiopharmaceutical $^{177}$Lu-PSMA I&T is provided, including in high purities with extended shelf life. Further provided are methods of synthesis of $^{177}$Lu-PSMA I&T and pharmaceutical compositions and methods of treatment that comprise $^{177}$Lu-PSMA I&T.

11 Claims, 4 Drawing Sheets

Auto-Scaled Chromatogram

Auto-Scaled Chromatogram

Auto-Scaled Chromatogram

Auto-Scaled Chromatogram

RADIOPHARMACEUTICAL AND METHODS

This application claims the benefit of U.S. provisional application No. 63/051,335 filed Jul. 13, 2020, incorporated by reference herein in its entirety.

FIELD

The radiopharmaceutical lutetium $^{177}$Lu-PSMA I&T including optically enriched mixtures thereof are provided, including in high purities with extended shelf life. Further provided are methods of synthesis of $^{177}$Lu-PSMA I&T including optically enriched mixtures thereof and pharmaceutical compositions that comprise $^{177}$Lu-PSMA I&T including optically enriched mixtures thereof.

BACKGROUND

Radiopharmaceuticals have been used for a variety of therapeutic and diagnostic indications. Among others, radiolabeled molecules have been useful to treat various malignant tumors.

Use of these agents presents certain challenges, including with respect to stability and shelf-life. In particular, therapeutic compositions comprising a radionuclide may undergo radiolysis during preparation and storage. During radiolysis, radionuclide emissions may react with other groups of the pharmaceutical agent thereby resulting in decomposition of the agent as well as undesired effects.

It thus would be desirable to have new radiopharmaceutical agents. It would be particularly desirable to have such agents that exhibit improved stability and purities.

SUMMARY

We now provide, inter alia, $^{177}$Lu-PSMA I&T having high purity, methods of preparing the compound, and pharmaceutical compositions and methods of treatment comprising $^{177}$Lu-PSMA I&T.

Still further, we have found additional methods for producing high purity $^{177}$Lu-PSMA I&T, including by at least substantially or completely excluding gentisate compounds from the reaction to form $^{177}$Lu-PSMA I&T.

We have also surprisingly found that addition of one or more gentisate compounds to the formed $^{177}$Lu-PSMA I&T can significantly enhance shelf life of the $^{177}$Lu-PSMA I&T, including maintaining high radiochemical purity over extended storage times.

In certain aspects, optically enriched mixtures of $^{177}$Lu-PSMA I&T are provided, including lutetium ($^{177}$Lu) zadavotide guraxetan.

$^{177}$Lu-PSMA I&T is a complex of lutetium ($^{177}$Lu) and EuK-Sub-kf-iodo-y-DOTAGA. The term "complex" herein generally refers to a union of $^{177}$Lu and the ligand EuK-Sub-kf-iodo-y-DOTAGA inclusive of chemical and physical variations that may exist with the joined or associated lutetium-177 and EuK-Sub-kf-iodo-y-DOTAGA (designated as $^{177}$Lu-PSMA I&T).

EuK-Sub-kf-iodo-y-DOTAGA and $^{177}$Lu-PSMA I&T each has several possible stereoisomers, including the R and S isomers of the carbon that is an N-ring substituent of the tetraazacyclotetradecane moiety of those compounds. References herein to EuK-Sub-kf-iodo-y-DOTAGA and $^{177}$Lu-PSMA I&T without further limitation includes all possible stereoisomers of each of those compounds and particularly both the noted R and S isomers.

In certain aspects, racemic mixtures of $^{177}$Lu-PSMA I&T and EuK-Sub-kf-iodo-y-DOTAGA are provided, including for use in the present pharmaceutical compositions and methods.

In other preferred aspects, optically enriched mixtures of $^{177}$Lu-PSMA I&T and EuK-Sub-kf-iodo-y-DOTAGA are provided, including for use in the present pharmaceutical compositions and methods.

In a preferred aspect, R isomer-enriched EuK-Sub-kf-iodo-y-DOTAGA is provided, i.e. EuK-Sub-kf-iodo-y-DOTAGA that is comprised of a weight excess of the R isomer (referring to the *carbon having N-ring substitution) of the following formula 1A:

1A

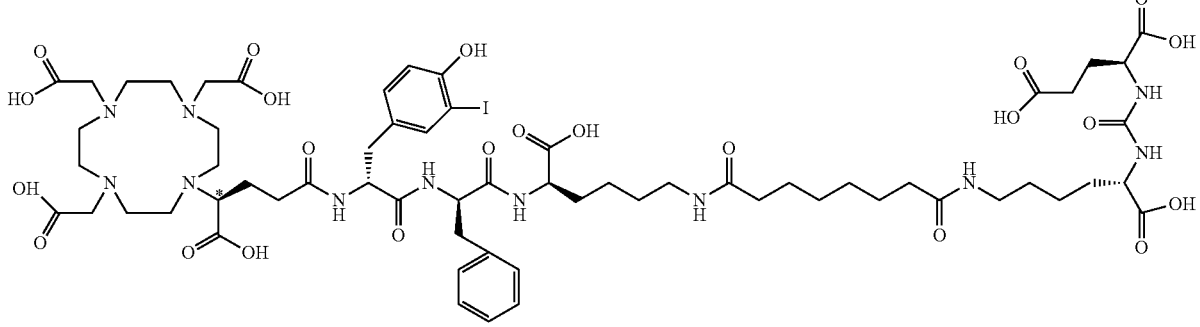

More particularly, we now provide $^{177}$Lu-PSMA I&T in high purities including for extended storage times. We also provide $^{177}$Lu-PSMA I&T in the absence of undesired impurities.

We also have found methods for producing $^{177}$Lu-PSMA I&T under comparatively reduced reaction times and/or temperatures. We also have found that such methods can produce $^{177}$Lu-PSMA I&T in enhanced purities.

In this aspect, generally preferred is EuK-Sub-kf-iodo-y-DOTAGA that is substantially optically enriched with the R isomer of formula 1A, or is an enantiomerically pure mixture of the R isomer of formula 1A.

In another aspect, S isomer-enriched EuK-Sub-kf-iodo-y-DOTAGA is provided, i.e. EuK-Sub-kf-iodo-y-DOTAGA that is comprised of a weight excess of the S isomer (referring to the *carbon having N-ring substitution) of the following formula 1B:

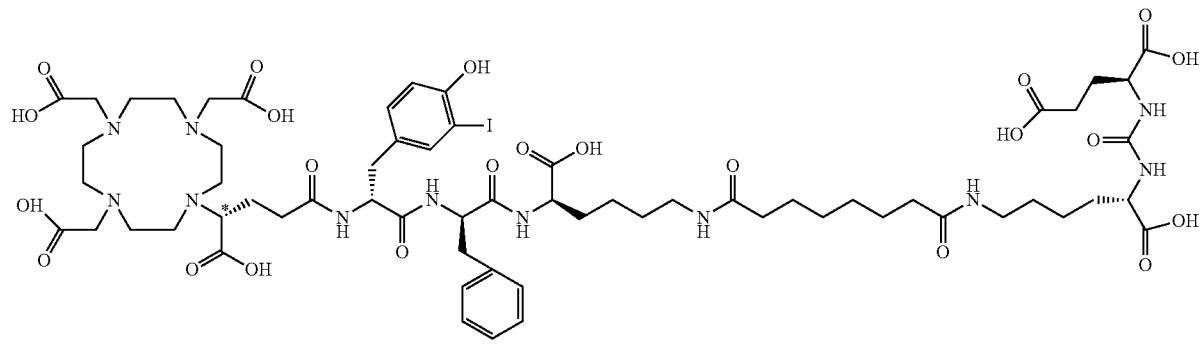

1B

In such aspect, generally preferred is EuK-Sub-kf-iodo-y-DOTAGA that is substantially optically enriched with the S isomer of formula 1B, or is an enantiomerically pure mixture of the S isomer of formula 11.

Additionally, in certain preferred aspects, the R isomer of $^{177}$Lu-PSMA I&T is provided, including for use in the present pharmaceutical compositions and methods. That R isomer is designated as lutein ($^{177}$Lu) zadavotide guraxetan and may be represented by the following structure 2A:

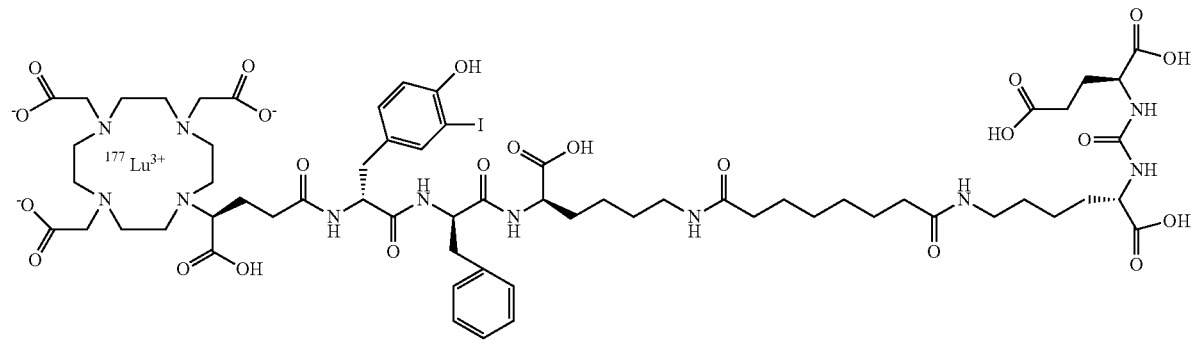

2A

In this aspect, generally preferred is $^{177}$Lu-PSMA I&T that is substantially optically enriched with the R isomer of formula 2A, or is an enantiomerically pure mixture of the R isomer of formula 2A In another aspect, the S isomer of $^{177}$Lu-PSMA I& T is provided, including for use in the present pharmaceutical compositions and methods. That S isomer may be represented by the following structure 213.

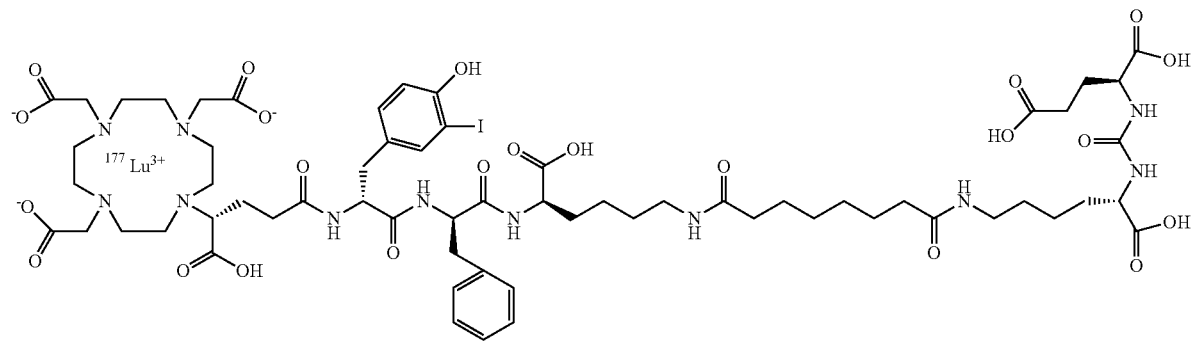

2B

In this aspect, generally preferred is $^{177}$Lu-PSMA I&T that is substantially optically enriched with the S isomer of formula 2B, or is an enantiomerically pure mixture of the S isomer of formula 2B.

The present $^{177}$Lu-PSMA I&T compound can exhibit particularly favorable chemical or radiochemical purities, including greater than 95, 96, 97, 98, 99, 99.5, 99.6, 99.7, 99.8 or 99.9 percent radiochemical purity and/or substantial absence of one or more prior impurities.

Thus, significantly, $^{177}$Lu-PSMA is now provided for the first time at the high purities as disclosed herein, including with the absence of prior impurities.

Additionally, new methods have been found to produce $^{177}$Lu-PSMA I&T with high (e.g., >99 or 99.5 molar percent) incorporation of lutetium-177. Surprisingly, the present methods can provide such high lutetium-177 incorporation under mild conditions, including reduced reaction times and/or reduced reaction temperatures.

More particularly, in one aspect, methods are provided for preparing $^{177}$Lu-PSMA I&T that include admixing lutetium-177 and EuK-Sub-kf-iodo-y-DOTAGA in the complete or substantial absence of one or more gentisate compounds.

It has been found that the at least substantial absence any gentisate compounds during the incorporation reaction (including heating) can substantially reduce impurities that would otherwise be produced through lutetium-177 incorporation. That is, it has been found that exclusion of any gentisate compounds from the reaction to incorporate lutetium-177 with EuK-Sub-kf-iodo-y-DOTAGA can produce lutetium $^{177}$Lu-PSMA I&T with reduced impurities. See, for instance, Example 1 which follows.

Gentisate compounds would be substantially absent (or an admixture comprising lutetium-177 and EuK-Sub-kf-iodo-y-DOTAGA would be substantially free of gentisate compound(s)) if one or more gentisate compounds are present in an amount of less than 10, 8, 5, 4, 3, 2, 1 or 0.5 weight percent relative to the weight amount of one or more other stabilizer compounds (including ascorbate compounds) present during an incorporation reaction.

As referred to herein, "the incorporation reaction" or similar term refers to the reaction to incorporate (e.g. complex) lutetium-177 with EuK-Sub-kf-iodo-y-DOTAGA to thereby produce $^{177}$Lu-PSMA I&T. In certain aspects, the incorporation reaction may include admixing lutetium-177 with EuK-Sub-kf-iodo-y-DOTAGA and heating the lutetium-177/EuK-Sub-kf-iodo-y-DOTAGA admixture.

Methods also are provided for preparing 177Lu-PSMA I&T that include admixing lutetium-177 and EuK-Sub-kf-iodo-y-DOTAGA in the presence of one or more ascorbate compounds suitably in an aqueous composition. The one or more ascorbate compounds may be referred to as a component of the "Reaction Composition" or similar term when added to or otherwise present with either lutetium-177 or EuK-Sub-kf-iodo-y-DOTAGA as part of the reaction to incorporate (e.g. complex) lutetium-177 with EuK-Sub-kf-iodo-y-DOTAGA to prepare lutetium $^{177}$Lu-PSMA I&T. The Reaction Composition is suitably an aqueous composition.

The Reaction Composition may comprise one or more other agents, particularly one or more distinct organic compounds in addition to ascorbate compound(s). Such additional distinct organic compounds sometimes are referred to herein as "stabilizer compounds."

In particular aspects, the EuK-Sub-kf-iodo-y-DOTAGA precursor (compound 1A and/or 1B) may be diluted before admixture with a lutetium-177 compound, such as diluting compound 1A and/or 1B with an aqueous composition preferably comprising one or more ascorbate compounds.

It has been found that the presence of one or more ascorbate compounds during the incorporation reaction (including heating) can substantially reduce impurities that would otherwise be produced through lutetium-177 incorporation.

In preferred systems, one or more ascorbate compounds are present during the incorporation reaction (including heating) together with at least substantial absence or preferably complete absence of one or more gentisate compounds during that incorporation reaction to reduce impurities that would otherwise be produced through lutetium-177 incorporation. In such an aspect, gentisate compound(s) would be substantially absent (or an admixture comprising lutetium-177, EuK-Sub-kf-iodo-y-DOTAGA and one or more ascorbate compounds would be substantially free of gentisate compound(s)) if one or more gentisate compounds were present in an amount of less than 10, 8, 5, 4, 3, 2, 1 or 0.5 weight percent relative to the weight amount of one or more ascorbate compounds present during an incorporation reaction.

It has been notably found that use of one or more ascorbate compounds particularly with a substantial or complete absence of one or more gentisate compounds during the incorporation reaction can avoid the occurrence or formation of an impurity having a retention time in the region of 10.2 minutes by high-performance liquid chromatography with a Waters XBridge BEH Phenyl-Hexyl Column, 130 Å, 3.5 m, 4.6 mm×150 mm using 0.1% trifluoracetic acid in water (Mobile Phase A) and 0.1% trifluoracetic acid in acetonitrile. A linear gradient from 85% Mobile Phase A to 55% Mobile Phase A over 12 minutes is used and the ratio is held for 15 minutes. As referred to herein, "an impurity having a retention time of 10.2 minutes by HPLC" or "an impurity having a retention time in the 9 to 11 minute region by HPLC" or similar term is assessed under the immediately above conditions, and the absence of such impurity would be demonstrated by a compound's spectra corresponding to the 9 to 12 minute region, in particular aspects the 9 or 9.5 to 10.5 or 11 minute region or the about 10.2 minute region as exemplified by the spectra of FIGS. 1C and 1D.

In a further aspect, suitably a composition (sometimes referred herein as the Formulation Composition and distinct from the Reaction Composition) is added following or upon termination of heating of the lutetium-177 and EuK-Sub-kf-iodo-y-DOTAGA particularly where a complex of lutetium-177 and EuK-Sub-kf-iodo-y-DOTAGA has been formed.

In particular, we have found enhanced stability and shelf-life of the formed $^{177}$Lu-PSMA I&T can be achieved by treatment of the incorporation reaction composition with one or more gentisate compounds following or upon termination of the reaction heating step.

Thus, methods are providing for preparing $^{177}$Lu-PSMA I&T, comprising a) admixing 1) lutetium-177 and 2) EuK-Sub-kf-iodo-y-DOTAGA; b) heating the admixed 1) lutetium-177 and 2) EuK-Sub-kf-iodo-y-DOTAGA, wherein a complex of lutetium-177 and EuK-Sub-kf-iodo-y-DOTAGA is formed; and c) adding one or more gentisate compounds while or after the heating is reduced or terminated. In certain aspects, both 1) one or more gentisate compounds and 2) one or more ascorbate compounds are added while or after the heating is reduced or terminated.

In a particular preferred embodiment, a gentisate compound is added to the formed complex of lutetium-177 and EuK-Sub-kf-iodo-y-DOTAGA promptly after the termination of the heating step, for example within 0.25, 0.5, 1 or 2 minutes of initiation of termination (complete removal of heating source, or the occurrence of an at least 20° C. temperature drop) of the lutetium-177 and EuK-Sub-kf-iodo-y-DOTAGA incorporation reaction.

In yet a further preferred embodiment, both 1) a gentisate compound and 2) an ascorbate compound are added to the formed complex of lutetium-177 and EuK-Sub-kf-iodo-y-DOTAGA promptly after the termination of the heating step, for example within 0.25, 0.5, 1 or 2 minutes of initiation of termination (complete removal of heating source, or the occurrence of an at least 20° C. temperature drop) of the lutetium-177 and EuK-Sub-kf-iodo-y-DOTAGA incorporation reaction.

In an additional embodiment, preferably an ascorbate compound is added to the formed complex of lutetium-177 and EuK-Sub-kf-iodo-y-DOTAGA promptly after the termination of the heating step, for example within 0.25, 0.5, 1 or 2 minutes of initiation of termination (complete removal of heating source, or the occurrence of an at least 20° C. temperature drop) of the lutetium-177 and EuK-Sub-kf-iodo-y-DOTAGA incorporation reaction.

Such a post-heating Formulation Composition may be an aqueous composition comprising one or more gentisate compounds and/or one or more ascorbate compounds.

In certain aspects, following the lutetium-177 incorporation reaction, the produced $^{177}$Lu-PSMA I&T may be first treated with one or more ascorbate compounds in the absence of a gentisate compound and subsequent to such ascorbate compound treatment the $^{177}$Lu-PSMA I&T may be treated (e.g. admixed) with one or more gentisate compounds. In other aspects, following the lutetium-177 incorporation reaction, the produced $^{177}$Lu-PSMA I&T may be treated with substantially simultaneously with one or more ascorbate compounds and one or more gentisate compounds. For instance, an aqueous formulation comprising both ascorbic acid or salt thereof or other ascorbate compound and gentisic acid or salt thereof or other gentisate compound may be added to the formed complex of lutetium-177 and EuK-Sub-kf-iodo-y-DOTAGA promptly after the termination of the heating step.

The aqueous admixture of the $^{177}$Lu-PSMA I&T and one or more gentisate compounds and optionally one or more ascorbate compounds can be stored until administration to a patient.

As discussed, it has been found that such post-incorporation reaction use of one or more gentisate compounds can provide enhanced stability and shelf life of the $^{177}$Lu-PSMA I&T. See, for instance, Example 1 which follows.

As referred to herein, an ascorbate compound or composition suitably may include for example ascorbic acid or an ascorbate salt such as sodium L-ascorbate, among others.

A gentisate compound or composition as referred to herein includes for example gentisic acid (2,5-dihydroxybenzoic acid). The term gentisate compound or composition also includes salts and esters of gentisic acid. A variety of gentisic acid salts may be suitably utilized as disclosed herein including for instance alkali metal, alkaline earth metal, and ammonium salts. Sodium and potassium salts may be preferred in some aspects. Ester compounds also may be utilized in certain aspects including for instance compounds esterified at one or both of the gentisic acid hydroxyl groups, such as compounds that have the 2-hydroxyl and/or 5-hydroxyl moieties functionalized with a methyl ester, ethyl ester or other $C_{1-6}$alkyl esters. In at least certain aspects, preferred gentisate compounds or compositions include gentisic acid or a gentisic acid salt.

In another aspect, methods are provided for preparing $^{177}$Lu-PSMA I&T that include admixing lutetium-177 and EuK-Sub-kf-iodo-y-DOTAGA; and heating the lutetium-177 and EuK-Sub-kf-iodo-y-DOTAGA admixture for less than 30 minutes, including 25 or 20 minutes or less. The lutetium-177 and EuK-Sub-kf-iodo-y-DOTAGA admixture suitably can be heated for even shorter periods such as up to or less than 18 minutes, or up to or less than 16, 15, 14, 13, 12, 11, 10, 9 or 8 minutes. In general heating for between 5 and 12 minutes can be suitable, at temperatures that include up to or less than 99° C., 98° C., 97° C., 96° C., 95° C., 94° C., 93° C., 92° C., 91° C. or 90° C. A reaction temperature of up to 40° C., 45° C., 50° C., 55° C., 60° C., 65° C., 70° C., 75° C., 80° C., 85° C., 90° C. or 95° C. may be suitable in certain aspects. Suitably, the lutetium-177 and EuK-Sub-kf-iodo-y-DOTAGA are heated as an aqueous mixture.

It has been found that such relatively mild reaction temperatures can provide high levels (e.g., at least 98, 99, 99.5 or 99.8 mole percent) incorporation of lutetium-177 and the precursor compound EuK-Sub-kf-iodo-y-DOTAGA (1A and/or 1B above) together with a reduced impurity profile. As noted, $^{177}$Lu-PSMA I&T (2A and/or 2B above) is now provided for the first time at the high purities as disclosed herein, including with the absence of prior impurities.

In preferred aspects, the incorporation of lutetium-177 and EuK-Sub-kf-iodo-y-DOTAGA includes at least one of the following 1), 2), 3) or 4) and preferably at least 1) and 2), more preferably at least 1), 2) and 3) and still more preferably each of the following 1), 2), 3) and 4):

1) inclusion of one or more ascorbate compound in the lutetium-177 incorporation reaction mixture. Optionally one or more gentisate compounds also may be present in the lutetium-177 incorporation reaction mixture, but such inclusion of gentisate compound is less preferred as discussed. Thus, particularly preferred is inclusion of one or more ascorbate compound in the lutetium-177 incorporation reaction mixture and without the inclusion of a gentisate compound;

2) a short heat treatment such up to or less than 30, 25, 20, 15, 12, 10 or 8 minutes as described above;

3) heating temperatures of the incorporation reaction mixture such as up to or less than 40° C., 45° C., 50° C., 55° C., 60° C., 65° C., 70° C., 75° C., 80° C., 85° C., 90° C. or 95° C.; and 4) a post-heating treatment (addition) with one or more gentisate compounds and/or one or more ascorbate compounds and preferably one or more gentisate compounds. Such treatments 1), 2), 3) and/or 4) can provide highly pure $^{177}$Lu-PSMA I&T (2A and/or 2B above) with notable absence of one or more prior impurities together with high levels of lutetium-177 incorporation. See, for instance, the results set forth in Example 1 which follows.

In a further aspect, pharmaceutical compositions are provided. Preferred pharmaceutical compositions including aqueous formulations that comprise a complex of lutetium-177 and EuK-Sub-kf-iodo-y-DOTAGA (particularly lutetium ($^{177}$Lu) zadavotide guraxetan, 2A above) in the high purities as disclosed herein.

Preferred pharmaceutical compositions also may be aqueous compositions that include 1) a complex of lutetium-177 and EuK-Sub-kf-iodo-y-DOTAGA (particularly lutetium ($^{177}$Lu) zadavotide guraxetan, 2A above) and 2) one or more ascorbate compounds. Preferred pharmaceutical compositions also include aqueous compositions that include 1) a complex of lutetium-177 and EuK-Sub-kf-iodo-y-DOTAGA (particularly lutetium ($^{177}$Lu) zadavotide guraxetan, 2A above) and 2) one or more gentisate compounds. Also preferred are aqueous compositions that include 1) a complex of lutetium-177 and EuK-Sub-kf-iodo-y-DOTAGA (particularly, lutetium ($^{177}$Lu) zadavotide guraxetan, 2A above) and 2) one or more ascorbate compounds and one or more gentisate compounds.

The one or more ascorbate compounds may be suitably present in a pharmaceutical composition in varying amounts, such as 5 or 10 mg/mL to 120 mg/mL; or 30 mg/mL to 100 mg/mL; or 40 mg/mL to 80 or 90 mg/mL. In a particular preferred aspect, the one or more ascorbate compounds such as an ascorbate salt may be present in an amount of 55 mg/mL to 75 mg/mL.

As discussed, the one or more ascorbate compounds may be incorporated both as a component of the lutetium-177 and EuK-Sub-kf-iodo-y-DOTAGA incorporation reaction as well as once the complex of lutetium-177 and EuK-Sub-kf-iodo-y-DOTAGA has been formed.

In such multiple additions to provide a desired amount of ascorbate compound(s) in a final $^{177}$Lu-PSMA I&T pharmaceutical composition, a Reaction Composition may contain one or more ascorbate compounds such as an ascorbate salt in an amount of 5 or 10 mg/mL to 120 mg/mL; or 5 or 10 mg/mL to 100 or 110 mg/mL; or 5 or 10 mg/mL to 80 or 90 mg/mL, in a particular preferred aspect, the one or more ascorbate compounds such as an ascorbate salt may be present in an amount of 55 mg/mL to 75 mg/mL.

Additionally, one or more ascorbate compounds such as an ascorbate salt may be added to a formed complex of lutetium-177 and EuK-Sub-kf-iodo-y-DOTAGA to provide a pharmaceutical formulation containing that formed complex wherein a total amount of ascorbate compound(s) is for example 5 or 10 mg/mL to 100 mg/mL in the formulation; or 5 or 10 mg/mL to 60 or 80 mg/mL in the formulation; or 5 or 10 mg/mL to 40 or 50 mg/mL in the formulation. In a particular preferred aspect, the one or more ascorbate compounds such as an ascorbate salt may be present in an amount of 55 mg/mL to 75 mg/mL in such formulation containing that formed complex of lutetium-177 and EuK-Sub-kf-iodo-y-DOTAGA.

In a pharmaceutical composition that contains a gentisate compound, one or more gentisate compounds suitably may be present such as gentisic acid or a gentisate salt in an amount of for example 5 or 10 mg/mL to 100 mg/mL; or 5 or 10 mg/mL to 60 or 80 mg/mL; or 5 or 10 mg/mL to 40 or 50 mg/mL. In a particular preferred aspect, the one or more gentisate compounds such as a gentisate salt may be present in an amount of 16 mg/mL to 36 mg/mL. As discussed, such amounts of one or more gentisate compounds may be preferably added to a formed complex of lutetium-177 and EuK-Sub-kf-iodo-y-DOTAGA while or after heating, in the heating step of the incorporation reaction, is reduced or terminated.

In the present pharmaceutical compositions, a complex of lutetium-177 and EuK-Sub-kf-iodo-y-DOTAGA (including, lutetium ($^{177}$Lu) zadavotide guraxetan, 2A above) also may be present in varying concentrations, such as to provide a volumetric radioactivity of at least 100 MBq/mL, preferably of at least 250, 300, 400, 500, 600, 700, 800, 900 or 1000 MBq/mL for 0.5, 1, 2, 3, 4 or 5 days following preparation of the pharmaceutical composition.

In certain aspects, a pharmaceutical composition does not contain a gentisate compound. In certain aspects, a pharmaceutical composition does not contain any other stabilizer agent other than one or more ascorbate compounds. Preferably, the radiochemical purity of a pharmaceutical composition is at least 95%, 96%, 97%, 98% or 99% for 3, 4 or 5 days or more at a temperature of 30° C. or less following preparation of the composition. Even more preferably, the radiochemical purity of a pharmaceutical composition is at least 96%, 97% or 98% for 3, 4 or 5 days or more at a temperature of 30° C. or less following preparation of the composition.

In a further aspect, a compound comprising a complex of lutetium-177 and EuK-Sub-kf-iodo-y-DOTAGA is provided, i.e. $^{177}$Lu-PSMA I&T such as lutetium ($^{177}$Lu) zadavotide guraxetan (2A above), wherein the complex is:

1) free of unchelated lutetium-177 in an amount of not more than 2, 1.5, 1.0 or 0.5 weight % based on total weight of the $^{177}$Lu-PSMA I&T, such as may be determined by radiometric detection (including HPLC radiometric detection); and/or 2) free of radiochemical impurities in an amount of not more than 5, 4, 3.5, 3, 2.5, 2, 1.5, 1.0 or 0.5 weight % based on total weight of the $^{177}$Lu-PSMA I&T, such as may be determined by radiometric detection (including HPLC radiometric detection); and/or 3) free of chemical impurities in an amount of not more than 5, 4, 3, 2, 1 or 0.5 weight %, all weight % based on total weight of the $^{177}$Lu-PSMA I&T, such as may be determined by HPLC/UV analysis, and where the $^{177}$Lu-PSMA I&T is maintained at 30° C. or less and such purity levels are exhibited for 3, 4 or 5 days or more following preparation of the $^{177}$Lu-PSMA I&T. Suitably, the compound may be present in an aqueous formulation. As understood, a radiochemical impurity will contain lutetium-177 or a degradation species thereof, while a chemical impurity may or may not contain lutetium-177 or a degradation species thereof. Amounts of radiochemical and chemical impurities as referred to herein can be assessed by chromatography including HPLC.

In a still further aspects, $^{177}$Lu-PSMA I&T (including 2A and/or 2B above) is provided as obtainable by or obtained from a process disclosed herein, including a process for the incorporation lutetium-177 and EuK-Sub-kf-iodo-y-DOTAGA comprising at least one of the following 1), 2) or 3) and preferably at least 1) and 2) and more preferably each of the following 1), 2) and 3):

1) inclusion of one or more ascorbate compound in the lutetium-177 incorporation reaction mixture. Optionally one or more gentisate compounds also may be present in the lutetium-177 incorporation reaction mixture, but such inclusion of gentisate compound is less preferred as discussed. Thus, particularly preferred is inclusion of one or more ascorbate compound in the lutetium-177 incorporation reaction mixture and without the inclusion of a gentisate compound;

2) a short heat treatment such up to or less than 30, 20, 15, 12, 10 or 8 minutes as described above; and 3) a post-heating treatment (addition) with one or more gentisate compounds and/or one or more ascorbate compounds and preferably one or more gentisate compounds.

Methods of treatment are also provided including to treat a subject that is suffering from a cell proliferative disease or disorder, particularly a cancer by administering to the subject an effective amount of $^{177}$Lu-PSMA I&T. In particular aspects, lutetium ($^{177}$Lu) zadavotide guraxetan is administered.

In particular, the present $^{177}$Lu-PSMA I&T and compositions, including lutetium ($^{177}$Lu) zadavotide guraxetan, may be used to treat a subject suffering from prostate cancer, including metastatic castration-resistant prostate cancer (such as may be manifested by progression of the disease despite prior surgical or chemical castration) including those subjects that have progressed following treatment with androgen receptor-axis-targeted (ARAT) therapies.

In a further aspect, kits are provided for $^{177}$Lu-PSMA I&T, including cold kits where the $^{177}$Lu-PSMA I&T can be prepared shortly before administration such as in a medical facility, for example a hospital laboratory or radiopharmacy. In such a kit, EuK-Sub-kf-iodo-y-DOTAGA (1A and/or 1B) may be provided in a vial or other container in lyophilized or other form separate from lutetium-177. The EuK-Sub-kf-iodo-y-DOTAGA and lutetium-177 are reacted as disclosed herein at the medical facility to provide $^{177}$Lu-PSMA I&T (including lutetium ($^{177}$Lu) zadavotide guraxetan) which then can be promptly administered to a patient. Such kits including cold kits may comprise components such as, for example, one or more buffering agents such as an acetate compound and/or one or more radioprotectants or stabilizer agents such as ascorbate compound and a gentisate compound.

In a yet further aspect, packaged preparations or products of $^{177}$Lu-PSMA I&T (including lutetium ($^{177}$Lu) zadavotide guraxetan)) are provided. A packaged preparation may comprise 1) $^{177}$Lu-PSMA I&T (including lutetium ($^{177}$Lu) zadavotide guraxetan) and optionally 2) instructions for using $^{177}$Lu-PSMA I&T (including lutetium ($^{177}$Lu) zadavotide guraxetan) for treating a cancer such as prostate cancer. Preferably, the packaged preparation will comprise a therapeutically effective amount of $^{177}$Lu-PSMA I&T (including lutetium ($^{177}$Lu) zadavotide guraxetan). The instructions suitably may be in written form, including as a packaging label. The $^{177}$Lu-PSMA I&T (including lutetium ($^{177}$Lu) zadavotide guraxetan) suitably may be contained within a lead vessel or other container that is within further packaging that may include product identification, instructions for use or other information.

Other aspects of the invention are disclosed infra.

BRIEF DESCRIPTION OF FIGURES

FIGS. 1A-1C show exemplary reactions with ascorbate and gentisate (peak at 10.2 min appears)—20 min reactions at 90° C. as detailed in Example 1 which follows.

DETAILED DESCRIPTION

Figure 1A:
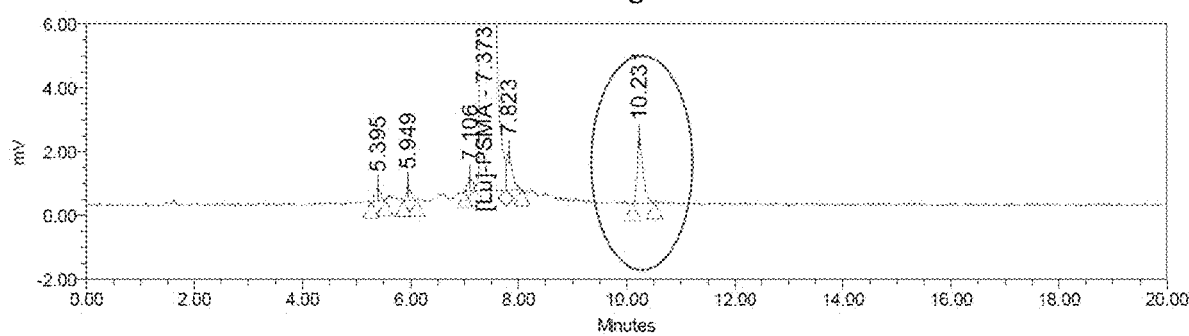
FIG. 1A shows an exemplary reaction with acetate and gentisate (peak at 10.2 min always appears)—20 min reactions at 90° C. min as detailed in Example 1 which follows.

In one aspect, methods for preparing $^{177}$Lu-PSMA I&T are provided that comprise: a) admixing 1) lutetium-177 and 2) EuK-Sub-kf-iodo-y-DOTAGA; and b) heating the admixed 1) lutetium-177 and 2) EuK-Sub-kf-iodo-y-DOTAGA for 15 minutes or less; wherein a complex of lutetium-177 and EuK-Sub-kf-iodo-y-DOTAGA is formed.

Preferably the admixed 1) lutetium-177 and 2) EuK-Sub-kf-iodo-y-DOTAGA are at least substantially free of a gentisate compound during the b) heating. Preferably, one or more ascorbate compounds are admixed with the 1) lutetium-177 and 2) EuK-Sub-kf-iodo-y-DOTAGA.

In further preferred aspects, the methods may further comprise adding one or more gentisate compounds to the complex of lutetium-177 and EuK-Sub-kf-iodo-y-DOTAGA, for example where such one more gentisate compounds are added upon reduction or termination of heat.

In still further preferred aspects, the methods may further comprise adding one or more gentisate compounds and/or one or more ascorbate compounds to the complex of lutetium-177 and EuK-Sub-kf-iodo-y-DOTAGA, for example where such one or more gentisate compounds and/or one or more ascorbate compounds are added upon reduction or termination of heat.

As discussed above, methods are also provided for preparing $^{177}$Lu-PSMA I&T, comprising a) admixing 1) lutetium-177 and 2) EuK-Sub-kf-iodo-y-DOTAGA; b) heating the admixed 1) lutetium-177 and 2) EuK-Sub-kf-iodo-y-DOTAGA, wherein a complex of lutetium-177 and EuK-Sub-kf-iodo-y-DOTAGA is formed; and c) adding one or more gentisate compounds while or after the heating is reduced or terminated. In certain aspects, both 1) a gentisate compound and 2) an ascorbate compound are added while or after the heating is reduced or terminated.

As discussed above, $^{177}$Lu-PSMA I&T is a lutetium-177 complex of the above compound 1A and/or 1B and may be represented by the following structure 2A and/or 21:

2A

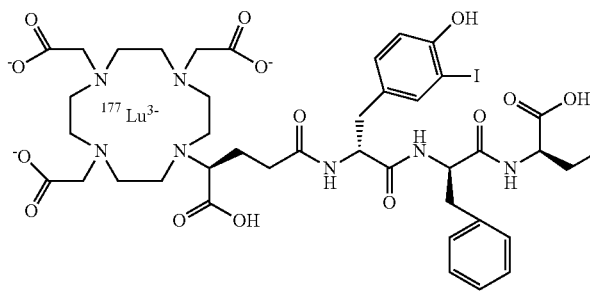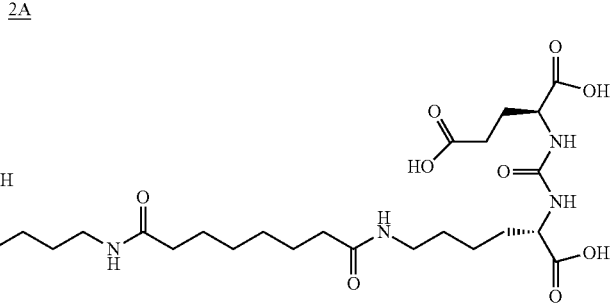

2B

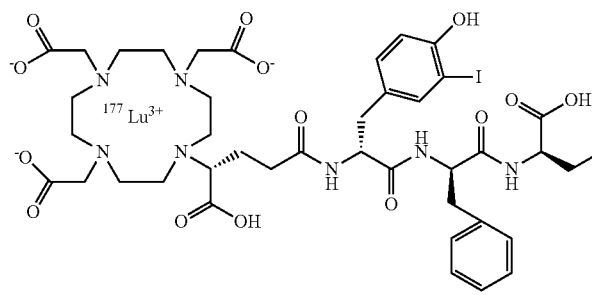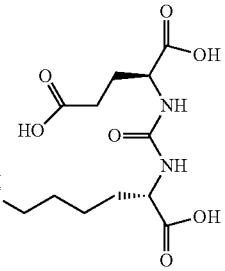

$^{177}$Lu-PSMA I&T also has a chemical name of suber-1-oyl-ε-(DOTA-GA-3-iodo-D-Tyr-D-Phe-D-Lys-OH)-8-oyl-ε-(HO-Glu-ureido-Lys-OH); lutetium-177(3+). $^{177}$Lu-PSMA I&T has a molecular formula of $C_{63}H_{89}{}^{177}LuIN_{11}O_2$ and molecular mass of 1672.29 g/mol.

The present invention, including compounds, methods, and pharmaceutical compositions/formulations will be described with reference to the following definitions which, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The language "and/or" is used herein as a shorthand notation to represent the expression "and," describing the combination of items, as well as "or," describing the items in the alternative form.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The term "about", as used herein, means an acceptable margin of error for a particular value, which depends in part on how the value is measured or determined. In certain embodiments, "about" as used herein will be understood by persons of ordinary skill in the art to mean up to plus or minus 20% of the particular term. In further embodiments, "about" as used herein will be understood by persons of ordinary skill in the art to mean up to plus or minus 10% of the particular term.

As used herein, the term "optically enriched" denotes the presence of one or more non-racemic stereoisomeric centers in a molecule, wherein the configuration of at least one stereoisomeric center has a predominance of one stereoisomeric configuration (R or S). For example, one stereoisomeric center in a molecule, typically a carbon atom, may have greater than 50 weight % (based on total weight of the compound) of its attached atoms spatially arranged in the (R) configuration. Alternatively, more than 50 weight % (based on total weight of the compound) may be spatially arranged in the (S) configuration. More preferably the molecule, or its stereoisomeric center, is substantially optically enriched, and even more preferably is substantially enantiomerically pure.

As used herein, the term "substantially optically enriched", when referring to a stereoisomer or stereoisomeric center, denotes that at least about 60 weight % (based on total weight of the compound), preferably about 70 weight % (based on total weight of the compound), more preferably about 80 weight % (based on total weight of the compound), still more preferably about 90 weight % (based on total weight of the compound) of one stereoisomer or one stereoisomeric center configuration predominates in the mixture, with at least about 95 weight % (based on total weight of the compound) of one stereoisomer or one stereoisomeric center configuration being even more preferred. In some preferred embodiments, the compound is "substantially enantiomerically pure", that is, at least about 97.5 weight % (based on total weight of the compound), more preferably about 99 weight % (based on total weight of the compound), even more preferably about 99.5 weight % (based on total weight of the compound) of one stereoisomeric configuration predominates.

As used herein, the term "substantially pure" means sufficiently homogeneous to appear free of readily detectable impurities as determined by standard analytical methods, such as thin layer chromatography (TLC), gel electrophoresis, high performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain embodiments, "substantially pure" refers to a collection of molecules, wherein at least about 55%, about 60%, about 65%, about 70%, about 75%, about 80%, about 85%, about 90%, about 95%, about 97%, about 98%, about 98.5%, about 99%, about 99.5% or about 99.9% or greater of the molecules are a single compound, including a racemic mixture or a single stereoisomer thereof, as determined by standard analytical methods.

As used herein, and unless otherwise specified, the terms "treat," "treating" and "treatment" refer to the eradication or amelioration of a disease, disorder, or condition, or of one or more symptoms associated with the disease, disorder or condition. In certain embodiments, the terms refer to minimizing the advancement or worsening of the disease, disorder, or condition resulting from the administration of a formulation of the invention to a patient with such a disease, disorder, or condition. In some embodiments, the terms refer to the administration of a formulation provided herein, after the onset of symptoms of the particular disease, disorder, or condition. The terms "treat," "treating", "treatment", or the like, as used herein covers the treatment of a disease, disorder, or condition in a subject, e.g., a mammal, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, preferably eliminating or curing of the disease, disorder, or condition. In a particular embodiment the terms "treat," "treating", "treatment", or the like, covers the treatment of a disease, disorder, or condition in a mammal, e.g., a primate, e.g., a human, and includes at least one of (i), (ii), and (iii) above. As is known in the art, adjustments for age, body weight, general health, sex, diet, time of administration, drug interaction and the severity of the condition may be necessary, and will be ascertainable with routine experimentation by one of ordinary skill in the art based on the invention described herein.

As used herein, the terms "subject", and "patient" are used interchangeably. The terms "subject" and "patient" refer to an animal such as a mammal including non-primates (e.g., a cow, pig, horse, sheep, rabbit, guinea pig, rat, cat, dog, and mouse) and primates (e.g., a monkey, chimpanzee and a human). Ina particular embodiment, the subject is a human.

Syntheses $^{177}$Lu-PSMA I&T (including lutetium ($^{177}$Lu) zadavotide guraxetan and including structures 2A and/or 2B below) can be prepared by complexing or incorporating $^{177}$Lu (lutetium-177) or halide thereof such as $^{177}$LuCl$_3$ with EuK-Sub-kf-iodo-y-DOTAGA (structure 1A and/or 1B below).

2A

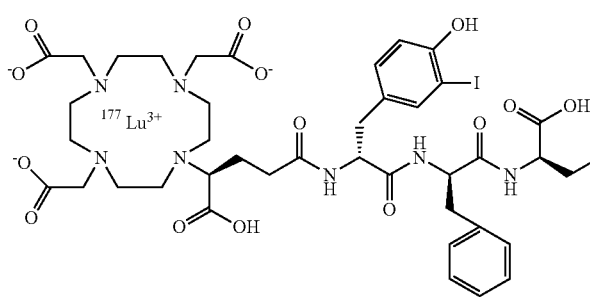
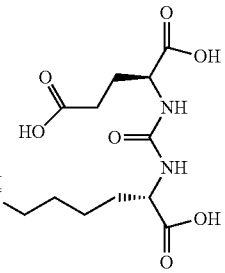

An IUPAC designation of compound 2A is lutetate(5-)-177Lu, [N-[(4R)-4-(carboxy-KO)-4-[4,7,10-tris[(carboxy-KO)methyl]-1,4,7,10-tetraazacyclododec-1-yl-KN1,KN4,KN7,KN10]-1-oxobutyl]-3-iodo-D-tyrosyl-D-phenylalanyl-N6-[8-[[[(5S)-5-carboxy-5-[[[[(1S)-1,3-dicarboxypropyl]amino]carbonyl]amino]pentyl]amino]-1,8-dioxooctyl]-D-lysinato(8-)]-, hydrogen (1:5); CAS Registry Number (CAS RN): 2447131-70-4).

2B

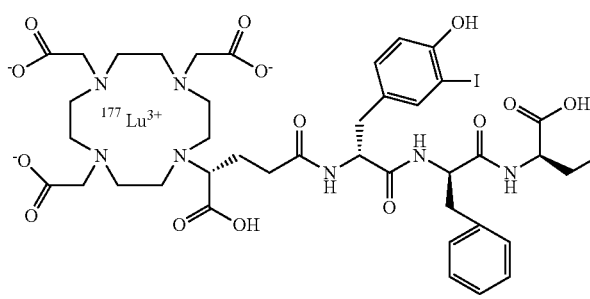
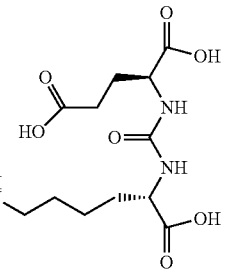

An IUPAC designation of compound 2B is lutetate(5-)-177Lu,N-[(4S)-4-(carboxy-KO)-4-[4,7,10-tris[(carboxy-KO)methyl]-1,4,7,10-tetraazacyclododec-1-yl-KN1,KN4,KN7,KN10]-1-oxobutyl]-3-iodo-D-tyrosyl-D-phenylalanyl-N6-[8-[[(5S)-5-carboxy-5-[[[[(1S)-1,3-dicarboxypropyl]amino]carbonyl]amino]pentyl]amino]-1,8-dioxooctyl]-D-lysinato(8-)]-, hydrogen (1:5).

It is understood that ¹⁷⁷Lu-PSMA I&T as referred to herein includes the above structure 2A and/or 2B as well as other complexes of lutetium (¹⁷⁷Lu) and EuK-Sub-kf-iodo-y-DOTAGA. For instance, references herein to ¹⁷⁷Lu-PSMA I&T include compounds that generally correspond to structure 2A and/or 2B but where the ¹⁷⁷Lu substantially complexes to other portions or moieties (such as one or more

1A

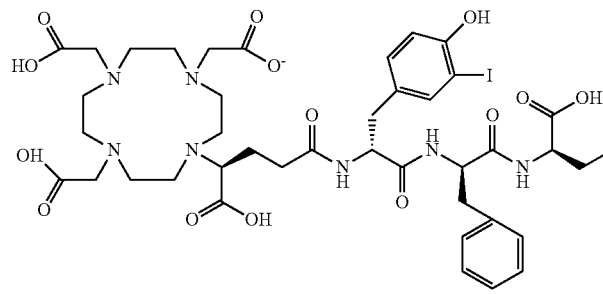

The R isomer compound of formula 1A has an IUPAC name of N-[(4R)-4-(carboxy-KO)-4-[4,7,10-tris[(carboxy-KO)methyl]-1,4,7,10-tetraazacyclododec-1-yl-KN1,KN4,KN7,KN10]-1-oxobutyl]-3-iodo-D-tyrosyl-D-phenylalanyl-N6-[8-[[(5S)-5-carboxy-5-[[[[(1S)-1,3-dicarboxypropyl]amino]carbonyl]amino]pentyl]amino]-1,8-dioxooctyl]-D-lysinato(8-)]-, hydrogen (1:5)).

other nitrogens) of the EuK-Sub-kf-iodo-y-DOTAGA molecule than as depicted in 2A and 2B above. References to ¹⁷⁷Lu-PSMA I&T also may include other stereoisomers than those shown in 1A, B, 2, and 2B above, although the stereoisomers depicted in 1A, 2, A, and 2B are preferred, particularly 1A and 2A (lutetium (¹⁷⁷Lu) zadavotide guraxetan).

1B

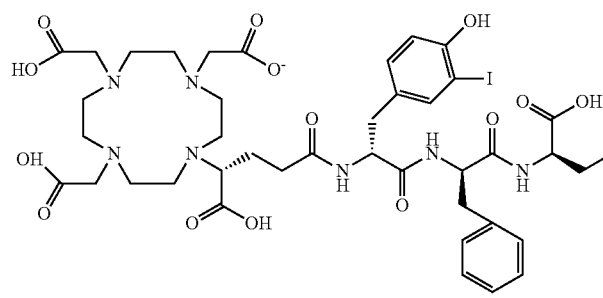

The S isomer compound of formula 1B has an IUPAC name of: [N-[(4S)-4-(carboxy-KO)-4-[4,7,10-tris[(carboxy-KO)methyl]-1,4,7,10-tetraazacyclododec-1-yl-KN1,KN4,KN7,KN10]-1-oxobutyl]-3-iodo-D-tyrosyl-D-phenylalanyl-N6-[8-[[(5S)-5-carboxy-5-[[[[(1S)-1,3-dicarboxypropyl]amino]carbonyl]amino]pentyl]amino]-1,8-dioxooctyl]-D-lysinato(8-)]-, hydrogen (1:5)).

The compound 1A and/or 1B may be suitably formed as described previously such as in Weineisen et al. *J Nucl Med* 2015; 56:1169-1176. To provide an optically enriched or enantiomerically pure sample of ¹⁷⁷Lu-PSMA I&T the corresponding optical isomer of EuK-Sub-kf-iodo-y-DOTAGA may be used in the incorporation reaction. That is, the compound of formula 1A may be reacted with lutetium-177 to provide the R isomer complex of formula 2A and the compound of formula 1B may be reacted with lutetium-177 to provide the S isomer complex of formula 2B.

To synthesize ¹⁷⁷Lu-PSMA I&T, lutetium-177 (¹⁷⁷Lu) can be admixed with EuK-Sub-kf-iodo-y-DOTAGA as discussed above. The ¹⁷⁷Lu suitably may be carrier added or more preferably no-carrier-added (n.c.a.) lutetium-177. To facilitate incorporation (e.g. complexing including chelating) of lutetium-177 with the EuK-Sub-kf-iodo-y-DOTAGA compound, preferably an admixture of the compounds is thermally treated.

As discussed, it has been found that substantially complete incorporation of lutetium-177 and EuK-Sub-kf-iodo-y-DOTAGA can be accomplished under comparatively mild conditions including relatively short heating times such as less than 30, 25, 20, 15, 12, 10 or 8 minutes and/or reduced temperatures such as up to or less than 99° C., 98° C., 97° C., 96° C., 95° C., 94° C., 93° C., 92° C., 91° C. or 90° C., or even lower temperatures for the incorporation reaction such as up to or less than 95° C., 90° C., 85° C., 80° C., 75° C., 70° C., 65° C., 60° C., 55° C., 50° C., 45° C. or 40° C. including for relatively short heating times such as up to or less than 30, 25, 20, 15, 12, 10 or 8 minutes.

In some embodiments, an admixture of lutetium-177 and EuK-Sub-kf-iodo-y-DOTAGA is heated for 20 minutes of less. In certain preferred embodiments, the admixture is heated for 15 minutes of less. In certain preferred embodiments, the admixture is heated for 12 minutes of less. In certain preferred embodiments, the admixture is heated for between about 8 and 12 minutes. For example, the admixture is heated for up to or less than about 8 minutes, for up to or less than about 9 minutes, for up to or less than about 10 minutes, for up to or less than about 11 minutes, or for up to or less than about 12 minutes. In certain preferred embodiments, the admixture is heated for at least about 8, 9, 10, 11 or 12 minutes.

In some embodiments, an admixture of lutetium-177 and EuK-Sub-kf-iodo-y-DOTAGA is heated at about 98° C. or less. In certain preferred embodiments, the admixture is heated at about 90° C. 5° C. For example, the admixture is heated at about 85° C., at about 86° C., at about 87° C., at about 88° C., at about 89° C., at about 90° C., at about 91° C., at about 92° C., at about 93° C., at about 94° C., or at about 95° C. Lower temperatures for the lutetium-177 incorporation also may be employed such as up to or less than 95° C., 90° C., 85° C., 80° C., 75° C., 70° C., 65° C., 60° C., 55° C., 50° C., 45° C. or 40° C. including as discussed above for relatively short heating times such as up to or less than 30, 25, 20, 15, 12, 10 or 8 minutes.

In some embodiments, a formulation including EuK-Sub-kf-iodo-y-DOTAGA and one or more ascorbate compounds is admixed with lutetium-177. In certain preferred embodiments, an acidic aqueous formulation of lutetium-177 is admixed with EuK-Sub-kf-iodo-y-DOTAGA and one or more ascorbate compounds (a Reaction Composition comprising one or more ascorbate compounds).

As referred to herein, an ascorbate compound suitably may include for example ascorbic acid or an ascorbate salt such as sodium L-ascorbate, among others.

In certain preferred embodiments, a hydrogen halide or acid halide aqueous formulation of lutetium-177 is admixed with EuK-Sub-kf-iodo-y-DOTAGA, including together with one more ascorbate compounds. In certain preferred embodiments, a hydrochloride acid aqueous formulation of lutetium-177 is admixed with EuK-Sub-kf-iodo-y-DOTAGA, including with one or more ascorbate compounds.

It is generally preferred that admixture of lutetium-177 and EuK-Sub-kf-iodo-y-DOTAGA is agitated during heat treatment, for example the admixture is stirred or shaken during a portion or substantially all of the heat treatment.

Figure 1B:
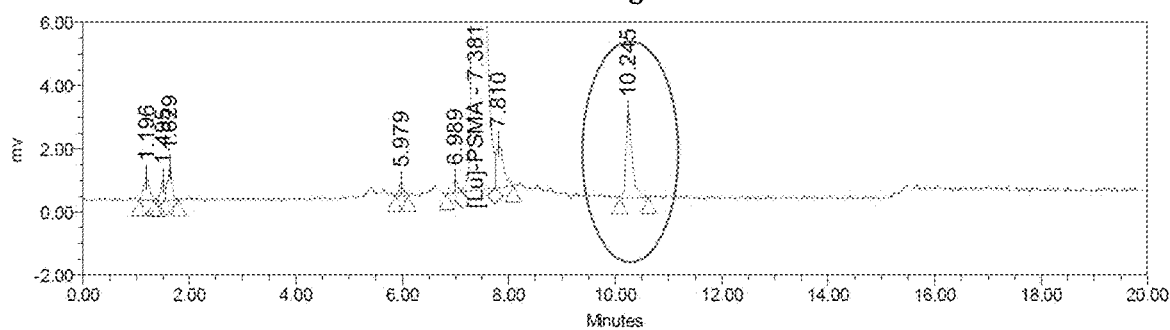
Figure 1C:
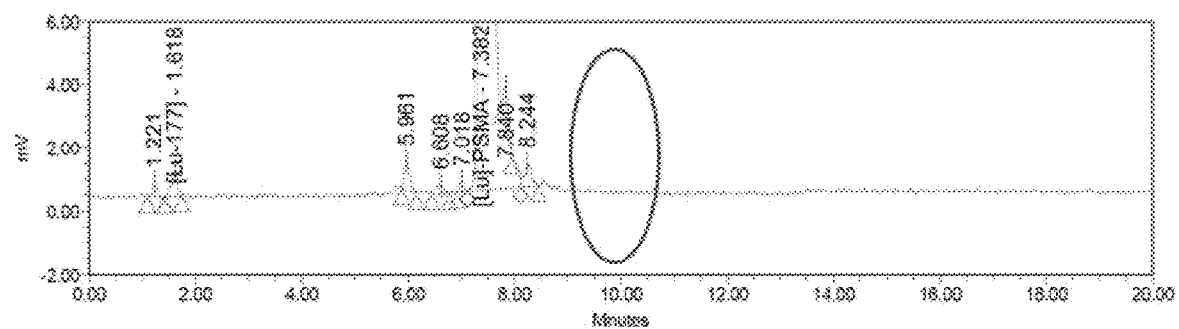
Figure 1D:
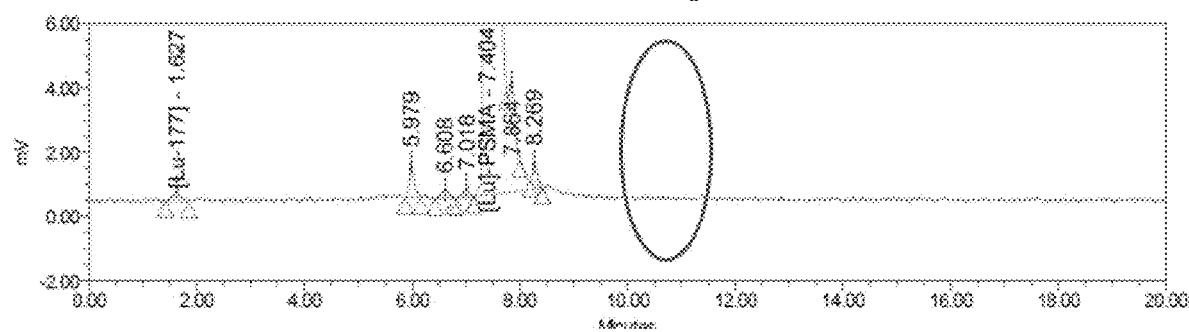
FIG. 1D shows an exemplary reaction with just ascorbate (peak at ~10.2 min never appears)—20 min reactions at 90° C. as detailed in Example 1 which follows.

In some embodiments, the produced complex of lutetium-177 and EuK-Sub-kf-iodo-y-DOTAGA does not contain a compound (impurity) that has a retention time of the 9 to 12 minute region, in particular aspects the 9 or 9.5 to 10.5 or 11 minute region or the about 10.2 minute region as shown in the spectra of FIGS. 1C and 1D and by HPLC analysis as defined herein, i.e. high-performance liquid chromatography with a Waters XBridge BEH Phenyl-Hexyl Column, 130 Å, 3.5 m, 4.6 mm×150 mm using 0.1% trifluoracetic acid in water (Mobile Phase A) and 0.1% trifluoracetic acid in acetonitrile, with a linear gradient from 85% Mobile Phase A to 55% Mobile Phase A being used over 12 minutes and the ratio was held for 15 minutes.

In some embodiments, the incorporation of lutetium-177 and EuK-Sub-kf-iodo-y-DOTAGA is greater than 98 mole percent. In certain preferred embodiments, the molar incorporation of lutetium-177 and EuK-Sub-kf-iodo-y-DOTAGA is greater than 99 mole percent, including 99.5, 99.6, 99.7, 99.8 and 99.9 mole percent.

In some embodiments, the radiochemical purity of the complex of lutetium-177 and EuK-Sub-kf-iodo-y-DOTAGA formulated as disclosed herein with one or more ascorbate compounds and optionally with one or more gentisate compounds is at least or up to 95%, 96%, 97% or 98% for 3, 4 or 5 days or more following the incorporation reaction and subsequent formulation with abscorbate compound(s) and optional gentisate compound(s) with storage of the $^{177}$Lu-PSMA I&T at a temperature of 30° C. or less.

Such levels of radiochemical purity and incorporation of lutetium-177 and EuK-Sub-kf-iodo-y-DOTAGA can be provided by the reaction product of the syntheses disclosed herein and formulation of such reaction product with one or more ascorbate compounds and optionally one or more gentisate compounds without further treatment (particularly purification) step such as chromatography. Thus, significantly, the formulated lutetium-177 incorporation reaction admixture can be directly packaged (for example, stored in a sealed vial or IV bag) following formulation of the incorporation reaction product with such high purity $^{177}$Lu-PSMA I&T without the need for a purification or other treatment step to remove impurities.

If desired however $^{177}$Lu-PSMA I&T prepared as disclosed herein may be further treated following incorporation of lutetium-177 and EuK-Sub-kf-iodo-y-DOTAGA, for example through HPLC or other chromatography or other purification treatment.

Preferred preparations of $^{177}$Lu-PSMA I&T may include one or more and preferably each of the following steps 1-6:

1. Provide lutetium-177 such as in a vial that can serve as a reaction vessel. The lutetium-177 suitably may be present in an aqueous acidic formulation, such as an HCl formulation.

2. Admix EuK-Sub-kf-iodo-y-DOTAGA with an aqueous buffer composition (Reaction Composition) that contains one or more ascorbate compound such as one or more of sodium L-ascorbate and ascorbic acid.

3. Admix the EuK-Sub-kf-iodo-y-DOTAGA composition from step 2 with the lutetium-177 formulation of step 1. For example, the EuK-Sub-kf-iodo-y-DOTAGA composition can be added to a vial that contains the lutetium-177.

4. The admixture of step 3 containing EuK-Sub-kf-iodo-y-DOTAGA and lutetium-177 then can be heated preferably with agitation, for example shaking with heating at 40-99° C. or 70-99° C., or 80-98° C. for up to 6, 7, 8, 9, 10, 11, 12, 13, 14, 15, 16, 17, 18, 19 or 20 minutes. Lower heating temperatures may be preferred, such as up to 40° C., 50° C., 60° C., 70° C., 80° C., 90° C. or 95° C. for up to 6, 7, 8, 9, 10, 11, 12, 13, 14, 15, 16, 17, 18, 19 or 20 minutes.

5. At the end of the heating treatment of step 4, an aqueous composition (Formulation Composition) containing one or more ascorbate compounds is added to the vial or other reaction vessel. For instance, within about 0.1, 0.25, 0.5, 1, 2, 3, 4 or 5 minutes after commencing reduction or termination of heating, an aqueous composition (Formulation Composition) containing one or more ascorbate compound is added to the vial or other reaction vessel. Reduction or termination of heating can include physical removal of the heating source from the reaction vessel, or termination of power to the heating element.

6. The admixture of step 5 then may be transferred to a vessel containing an aqueous composition that comprises one or more ascorbate compounds and, in certain systems, one or more gentisate compounds. The mixture may be filtered and transferred to a container such as a syringe, vial or IV bag. Desired dosages can be dispensed for administration to a patient preferably within 5, 4, or 3 days from completing step 5 above.

Pharmaceutical Compositions

In a further aspect, pharmaceutical compositions are provided. Preferred pharmaceutical compositions may include an aqueous composition including 1) a complex of lutetium-177 and EuK-Sub-kf-iodo-y-DOTAGA and 2) one or more ascorbate compounds. Particularly preferred pharmaceutical compositions may include an aqueous composition including 1) a complex of lutetium-177 and EuK-Sub-kf-iodo-y-DOTAGA and 2) one or more ascorbate compounds. Preferably, the radiochemical purity of the composition is at least 95%, 96%, 97%, 95% or 99% where the composition is maintained at 30° C. or less and for 3, 4 or 5 days or more following preparation of the composition.

In certain preferred embodiments, the pharmaceutical composition is free of unchelated lutetium-177 in an amount of not more than 2, 1.5, 1.0 or 0.5 weight % based on total weight of the pharmaceutical composition, such as may be determined by radiometric detection (including HPLC radiometric detection), where the composition is maintained at 30° C. or less and such purity levels are exhibited for 3, 4 or 5 days or more following preparation of the composition.

In additional preferred embodiments, the pharmaceutical composition is free of radiochemical impurities in an amount of not more than 5, 4, 3.5, 3, 2.5, 2, 1.5, 1 or 0.5 weight % based on total weight of the pharmaceutical composition, such as may be determined by radiometric detection (including HPLC radiometric detection), where the composition is maintained at 30° C. or less and such purity levels are exhibited for 3, 4 or 5 days or more following preparation of the composition.

In yet still additional preferred embodiments, the pharmaceutical composition is free of chemical impurities in an amount of not more than 5, 4, 3, 2, 1 or 0.5 weight % based on total weight of the pharmaceutical composition, such as may be determined by chromatography or other method including HPLC or HPLC/UV analysis, where the composition is maintained at 30° C. or less and such purity levels are exhibited for 3, 4 or 5 days or more following preparation of the composition.

In yet still additional preferred embodiments, the pharmaceutical composition is 1) free of unchelated lutetium-177 in an amount of not more than 2, 1.5, 1.0 or 0.5 weight % (such as may be determined by radiometric detection (including HPLC radiometric detection)); 2) free of radiochemical impurities in an amount of not more than 5, 4, 3.5, 3, 2.5, 2, 1.5, 1 or 0.5 weight % (such as may be determined by radiometric detection (including HPLC radiometric detection); and 3) free of chemical impurities in an amount of not more than 5, 4, 3, 2, 1 or 0.5 weight % (such as may be determined by HPLC/UV analysis), with all weight % based on total weight of the pharmaceutical composition, and where the composition is maintained at 30° C. or less and such purity levels are exhibited for 3, 4 or 5 days or more following preparation of the composition.

In certain embodiments, the pharmaceutical composition is formulated for parenteral administration, such as intravenous, intramuscular, intradermal, subcutaneous, intrathecal or intraperitoneal administration. For example, the pharmaceutical composition is formulated for intravenous, intramuscular, subcutaneous or intradermal injection. In preferred aspects, the pharmaceutical composition is formulated for intravenous administration. In typical embodiments, the pharmaceutical composition may be administered in a form of a pharmaceutical aqueous solution.

In certain embodiments, the pharmaceutical composition is an aqueous solution, dispersion or other admixture such as for injection and comprises $^{177}$Lu-PSMA I&T (including lutetium ($^{177}$Lu) zadavotide guraxetan) and preferably one or more ascorbate compounds. In further preferred embodiments, the pharmaceutical composition is an aqueous solution, dispersion or other admixture such as for injection and comprises 1) $^{177}$Lu-PSMA I&T including lutetium ($^{177}$Lu) zadavotide guraxetan) and preferably one or more ascorbate compounds and one or more gentisate compounds.

In certain preferred embodiments, a pharmaceutical aqueous solution, dispersion or admixture is provided that includes: 1) a complex of lutetium-177 and EuK-Sub-kf-iodo-y-DOTAGA; and 2) at least one stabilizer compound that preferably can inhibit radiolytic degradation of the composition during storage following preparation of the complex. $^{177}$Lu-PSMA I&T is suitably present in a concentration that it provides a volumetric radioactivity of at least 100 MBq/mL, preferably of at least 250, 500, 750 or 1000 MBq/mL within 1, 2, 3, 4 or 5 days following preparation. In certain aspects, $^{177}$Lu-PSMA I&T is present in a concentration that it provides a volumetric radioactivity of from 100 to 1000 MBq/mL, preferably from or up to about 250, 500, 750 or 1000 MBq/mL within 1, 2, 3, 4 or 5 days following preparation.

In certain aspects, the one or more stabilizer compounds may be present in a total concentration of at least 5 mg/mL, preferably at least 10 mg/mL of an aqueous pharmaceutical composition.

In certain aspects, the one or more stabilizer compounds are one or more of gentisic acid (2,5-dihydroxybenzoic acid) or salts thereof, ascorbic acid (L-ascorbic acid) or salts thereof (e.g. sodium ascorbate), methionine, histidine, melatonine, N-acetylmethionine, ethanol, or Se-methionine, preferably ascorbic acid or salts thereof and gentisic acid or salts thereof.

In certain aspects, the pharmaceutical aqueous formulation has a shelf life of at least 24 hours at about 30° C. or less, at least 48 hours at about 30° C. or less, at least 72 hours at 30° C. or less, or from 24 hours to 120 hours at 30° C. or less, from 24 hours to 96 hours at 30° C. or less, from 24 hours to 84 hours at 30° C. or less, from 24 hours to 72 hours at 30° C. or less, in particular a shelf life of 72 hours at 30° C. or less.

In certain aspects, one, two or three total distinct stabilizer compounds are present during the complex formation of lutetium-177 and EuK-Sub-kf-iodo-y-DOTAGA, preferably in an amount to result in a concentration of from 5 mg/mL or more of the 1-3 stabilizer compounds. As discussed, preferably at least one of the stabilizer compounds will be an ascorbate compound.

In certain aspects, as discussed, one or more stabilizer compounds may be added after formation of the complex of lutetium-177 and EuK-Sub-kf-iodo-y-DOTAGA, for example upon completion of heating of an admixture of lutetium-177 and EuK-Sub-kf-iodo-y-DOTAGA. As discussed, preferably at least one of the stabilizer compounds added after formation of $^{177}$Lu-PSMA I&T will be an ascorbate compound, for example where such stabilizer compound(s) are added upon temperature reduction/termination at the conclusion of a heating step. In certain aspects, a gentisate compound also will be added after formation of $^{177}$Lu-PSMA I&T, for example where such stabilizer compound(s) are added upon temperature reduction/termination at the conclusion of a heating step. As discussed, reduction or termination of temperature or heating can include physical removal of the heating source from the reaction vessel, or termination of power to the heating element.

In certain embodiments, a pharmaceutical aqueous solution may further include a sequestering agent, for example added after formation of a complex lutetium-177 and EuK-Sub-kf-iodo-y-DOTAGA, suitably to remove uncomplexed lutetium-177. Suitable sequestering agents may include for example diethylentriaminepentaacetic acid (DTPA) or a salt thereof, suitably in an amount to result in a concentration of from 0.01 to 0.50 mg/mL of the aqueous $^{177}$Lu-PSMA I&T composition.

In a particularly preferred aspect, $^{177}$Lu-PSMA I&T is provided as a sterile solution for intravenous use. The $^{177}$Lu-PSMA I&T solution suitably may be clear, colorless to slightly yellow. A single-dose vial suitably will contain 6.8+/−10% GBq $^{177}$Lu-PSMA I&T for example calibrated at 1, 2, 3 or more days post-day of manufacture in 10 to 14 mL formulated with radioprotectants and may include a buffer. The pH range of the solution is preferably 5.0 to 7.0.

Methods of Treatment

As discussed, use of $^{177}$Lu-PSMA I&T (including 2A and/or 2B above) is provided to treat cancers, including prostate cancer, for example non-metastatic prostate cancer and metastatic prostate cancer, including hormone sensitive prostate cancer, castration resistant prostate cancer (CRPC) and drug-resistant prostate cancer, such as anti-androgen drug (e.g., enzalutamide) resistant prostate cancer.

In such methods, $^{177}$Lu-PSMA I&T (including 2A and/or 2B above) can be administered to a subject such as a human in an amount effective to treat the cancer (e.g., reduction of tumor size), such as at a dose of about 0.1 GBq to about 30 GBq be suitably administered from a unit dose in a vial or a syringe or as a bulk solution in a vial or a syringe prepared from a cold-kit prepared with lutuetium-177 at a local or central radiopharmacy or through cGMP central manufacturing.

In certain embodiments, the subject is suffering from prostate cancer such as one or more of castration-sensitive prostate cancer, castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer), docetaxel-resistant prostate cancer, AR-V7-induced drug-resistant prostate cancer such as AR-V7-induced enzalutamide-resistant prostate cancer, AKR1C3-induced drug-resistant prostate cancer such as AKR1C3-induced enzalutamide-resistant prostate cancer, and combinations thereof.

In particular embodiments, the subject is a human suffering metastatic castration-resistant prostate cancer and an effective amount of $^{177}$Lu-PSMA I&T (including lutetium ($^{177}$Lu) zadavotide guraxetan) is administered to the subject to treat the prostate cancer.

In further particular embodiments, the subject is a human suffering metastatic castration-resistant prostate cancer and an effective amount of $^{177}$Lu-PSMA I&T including lutetium ($^{177}$Lu) zadavotide guraxetan) is administered to the subject to treat the prostate cancer.

The effective amount of $^{177}$Lu-PSMA I&T (including lutetium ($^{177}$Lu) zadavotide guraxetan) radiopharmaceutical administered to a patient will generally be determined by considering the patient record. However, the effective amount suitably may be within a range of about 0.1 GBq to 30 GBq per dose. More specifically, the dose may range from about 1 GBq to about 20 GBq or about 30 GBq per dose subject, for example, about 1, 1.5, 2, 2.5, 3, 3.5, 4, 4.5, 5, 5.5, 6, 6.5, 6.8, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21.5, 22, 22.5, 23, 23.5, 24, 24.5, 25, 25.5, 26, 26.5, 27, 27.5, 28, 28.5, 29, 29.5 or 30 GBq per dose of $^{177}$Lu-PSMA I&T (including lutetium ($^{177}$Lu) zadavotide guraxetan), or any range between two of the above values. The dose can be administered from a unit dose in a vial or a syringe or as a bulk solution in a vial or a syringe prepared from a cold-kit prepared with lutetium-177 at a local or central radiopharmacy or through cGMP central manufacturing.

If necessary or desirable, the treatment may involve more than one administration of an effective amount of $^{177}$Lu-PSMA I&T (including lutetium ($^{177}$Lu) zadavotide guraxetan). It is generally beneficial to repeat the administration of $^{177}$Lu-PSMA I&T (including lutetium ($^{177}$Lu) zadavotide guraxetan) to the subject after 7 to 56 days, such as at a 4 to 8 week interval.

In a particularly preferred protocol, the $^{177}$Lu-PSMA I&T (including lutetium ($^{177}$Lu) zadavotide guraxetan) dosage form is a sterile aqueous solution that is administered by intravenous injection. The dosing regimen may include multiple infusions such as 1, 2, 3, 4, 5, 6, 7, 8, 9 or 10 infusions at effective dosages such as of 6.8 GBq+/−10% each, administered about 1, 2, 3, 4, 5, 6, 7, 8, 9 or 10 weeks apart.

Combination Therapy $^{177}$Lu-PSMA I&T (including 2A and/or 2B above) suitably may be administered to a subject in conjunction or combination with one or more other therapeutic agents, particularly one or more other chemotherapeutic agents.

In one aspect, a subject may receive treatment with $^{177}$Lu-PSMA I&T (including 2A and/or 2B above) in combination with a regime of docetaxel and/or prednisone, particularly for a subject suffering from castration resistant prostate cancer.

In another aspect, a subject may receive treatment with $^{177}$Lu-PSMA I&T (including 2A and/or 2B above) in combination with a regime that can include chemotherapy such as docetaxel; cisplatin; gemcitabine; cisplatin/gemcitabine; cabazitaxel; one or more antiandrogens such as one or more LHRH agonists, such as leuprolide and goserelin, or antagonists; one or more antiandrogens such as flutamide, nilutamide, bicalutamide, cyproterone, abiraterone, enzalutamide, darolutamide and apalutamide; one or more PARP inhibitors such as olaparib, rucaparib or niraparib, particularly for a subject suffering from prostate cancer including metastatic castration resistant prostate cancer.

In additional aspects, a subject may receive treatment with $^{177}$Lu-PSMA I&T (including 2A and/or 2B above) in combination with an immunotherapy regime which may include adoptive cell therapies or adoptive immunotherapy.

For example, to treat a patient suffering from cancer, $^{177}$Lu-PSMA I&T (including 2A and/or 2B above) may be administered in combination with immune effector cells (e.g., T cells, NK cells) engineered to express a Chimeric Antigen Receptor (e.g. CAR T-cell therapy), including to treat a cancer or a disease associated with expression of a tumor antigen.

For a patient suffering from cancer including prostate cancer, $^{177}$Lu-PSMA I&T (including 2A and/or 2B above) also may be administered in combination with other immune-based therapies such as sipuleucel-T (Provenge) or other immune-boosting approaches including antibody treatments. For instance, in one protocol, $^{177}$Lu-PSMA I&T (including 2 and/or 2B above) may be administered in combination with one or more monoclonal antibodies such as ipilimumab (Yervoy) and/or nivolumab (Opdivo) for treating a patient suffering from cancer, particularly prostate cancer.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject in need of treatment as disclosed herein. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

Packaged $^{177}$Lu-PSMA I&T and Kits

As discussed above, treatment kits are also provided, including cold kits where the $^{177}$Lu-PSMA I&T (including 2A and/or 2B above) can be prepared shortly before administration such as in a medical facility, for example a hospital laboratory or radiopharmacy. In such a kit, EuK-Sub-kf-iodo-y-DOTAGA may be provided in a vial or other container in lyophilized or other form separate from lutetium-177. The EuK-Sub-kf-iodo-y-DOTAGA and lutetium-177 are reacted as disclosed herein at the medical facility to provide $^{177}$Lu-PSMA I&T (including 2A and/or 2B above) which then can be promptly administered to a patient.

In a further aspect, packaged preparations or products of $^{177}$Lu-PSMA I&T (including 2A and/or 2B above) are also provided. A packaged preparation may comprise 1)$^{177}$Lu-PSMA I&T and optionally 2) instructions for using $^{177}$Lu-PSMA I&T for treating a cancer such as prostate cancer. Preferably, the packaged preparation will comprise a therapeutically effective amount of $^{177}$Lu-PSMA I&T (including 2A and/or 2B above).

In certain exemplary packaged preparations or products, $^{177}$Lu-PSMA I&T (including 2A and/or 2B above) suitably can be packaged in suitable containers labeled, for example, for use as a therapy to treat a subject suffering from prostate cancer. The containers can include $^{177}$Lu-PSMA I&T and suitably one or more ascorbate compounds and one or more gentisate compounds as disclosed herein. A product can include a container (e.g., a vial or the like) containing $^{177}$Lu-PSMA I&T. In addition, an article of manufacture or kit further may include, for example, packaging materials, instructions for use, syringes, delivery devices, for treating the targeted condition, such as prostate cancer or other cancer.

A packaged system or product may also include a legend (e.g., a printed label or insert or other medium (e.g., an audio or video file) describing the product's use). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents.

The following non-limiting examples are illustrative.

Example 1

Radiolabeling was performed using no-carrier added $^{177}$LuCl$_3$. Radiolabeling was done either directly in the isotope vial, or transferred to a 20 mL vial. $^{177}$Lu-PSMA-I&T is prepared as described in Weineisen et al. *J Nucl Med* 2015; 56:1169-1176 by use of racemic EuK-Sub-kf-iodo-y-DOTAGA. Lutetium ($^{177}$Lu) zadavotide guraxetan is also prepared as described in Weineisen et al. *J Nucl Med* 2015; 56:1169-1176 using the R-isomer of EuK-Sub-kf-iodo-y-DOTAGA (i.e. the compound of formula 1A above). The racemic $^{177}$Lu-PSMA-I&T or optically enriched lutetium ($^{177}$Lu) zadavotide guraxetan was diluted using reaction buffer and was added to a reaction vial to form a Reaction Composition. A thus prepared Reaction Composition was heated with mixing using a shaker at 90+/−4° C. Different reaction times and cool down periods were tested during development, ranging from 10 to 30 mins of labelling time and 0 to 20 mins of cool down time. Three different Reaction Compositions ((A), (B) and (C) set forth below) were assessed.

The formulated racemic $^{177}$Lu-PSMA-I&T and optically enriched lutetium ($^{177}$Lu) zadavotide guraxetan batches were sampled for quality control testing and tested for stability for up to 6 days post-day of manufacture. Batches of both $^{177}$Lu-PSMA-I&T and lutetium ($^{177}$Lu) zadavotide guraxetan at room temperature (25° C.) and 2-8° C. storage were evaluated during development. Reverse-phase HPLC with radiometric and UV detection and thin layer chromatography with radiometric detection were used to assess chemical and radiochemical impurities.

(1) Reaction Compositions Evaluated:

(A) 99 to 247 mg/mL Ascorbate (pH 4.5 to 6), made from sodium L-ascorbate and ascorbic acid (preferred condition 162 mg/mL, pH 5.5 to 6.0)

(B) 5.1 to 12.5 mg/mL Gentisic Acid (0.4 M acetate used as buffer, pH5-6.5), made from gentisic acid (C) 100 mg/mL Ascorbate with 5.0 mg/mL Gentisic Acid (pH 5-6.5), made from sodium L-ascorbate, ascorbic acid and gentisic acid (2) Formulation Compositions Evaluated:

(A) 65 to 68 mg/mL Ascorbate with 25 to 28 mg/mL Gentisic Acid (pH6-7), made from sodium L-ascorbate and gentisic acid (preferred condition)

(B) 64 to 86 mg/mL Ascorbate (pH 6-7), made from sodium L-ascorbate

The conditions as set forth in the following Table 1 were evaluated:

TABLE 1

| | Reaction Compositions | | | | Formulation Compositions | | Radioactivity Concentration at Activity Reference Time |
|---|---|---|---|---|---|---|---|
| | Gentisic Acid | Ascorbate | Acetate (buffer) | Reaction Time (Min) | Gentisic Acid | Ascorbate | |
| Experiment 1 | + | − | + | 30 | − | + | 0.93 |
| Experiment 2 | + | − | + | 30 | − | + | 0.97 |
| Experiment 3a | + | − | + | 20 | − | + | 0.53 |
| Experiment 3b | + | − | + | 20 | + | + | 0.48 |
| Experiment 3c | + | + | − | 20 | − | + | 0.58 |
| Experiment 3d | + | + | − | 20 | + | + | 0.56 |
| Experiment 4a | − | + | − | 20 | + | + | 0.49 |
| Experiment 4b | − | + | − | 20 | + | + | 0.49 |
| Experiment 4c | + | + | − | 20 | + | + | 0.49 |
| Experiment 4d | + | + | − | 20 | + | + | 0.49 |
| Experiment 5a | + | − | + | 20 | + | + | 0.49 |
| Experiment 5b | − | + | − | 20 | + | + | 0.49 |
| Experiment 6a | + | − | + | 20 | + | + | 0.49 |
| Experiment 6b | − | + | − | 20 | + | + | 0.49 |
| Experiment 7 | − | + | − | 20 | + | + | 0.49 |
| Experiment 8 | − | + | − | 15 | + | + | 0.49 |
| Experiment 9 | − | + | − | 10 | + | + | 0.49 |
| Experiment 10 | − | + | − | 10 | + | + | 0.49 |
| Experiment 11 | − | + | − | 10 | + | + | 0.49 |
| Experiment 12 | − | + | − | 10 | + | + | 0.49 |

In each of Examples 1, 2, 3a, 3b, 3c, 3d, 4a, 4b, 4c and 4d, racemic EuK-Sub-kf-iodo-y-DOTAGA and racemic $^{177}$Lu-PSMA I&T was used. In each of Examples 5a, 5b, 6a, 6b, 7, 8, 9, 10, 11 and 12R-isomer enriched EuK-Sub-kf-iodo-y-DOTAGA (LA above) and lutetium ($^{177}$Lu) zadavotide guraxetan (2A) was used. Results:

1. Lu-177 Incorporation:

Chromatography shows the amount of Lu-177 incorporated into the EuK-Sub-kf-iodo-y-DOTAGA was >99.5% for all reactions at completion of production. This demonstrates that under all conditions, including a reaction time limited to 10 minutes, full incorporation of Lu-177 into EuK-Sub-kf-iodo-y-DOTAGA was achieved. The ability to incorporate Lu-177 in a reduced time, reduced the number of impurities at the end of production.

2. Negative Impact of Gentisic Acid in the Reaction Composition (Incorporation Reaction):

In each of Experiments 1 and 2, gentisic acid was present in the Reaction Composition, but the amount of gentisic acid present in the Reaction Composition was double in Example 2 relative to Example 1. Specifically, in Experiment 1, 6.6 mg/mL of gentisic acid was used in the Reaction Composition; and in Experiment 2, 12.5 mg/mL of gentisic acid was used in the Reaction Composition. Over the 5 or 6 day evaluation period, it was found that radiochemical purity dropped 5% for the Experiment 1 sample and radiochemical purity dropped 13% for the Experiment 2 sample.

Experiments 3 through 6 demonstrated that the inclusion of only gentisic acid in the reaction results in an impurity peak that elutes at ~10.2 min; this peak is absent when only ascorbate is used. When gentisic acid and ascorbate are both used in the reaction, the peak at ~10.2 min also may be present (see FIGS. 1A-1D) in certain instances. Therefore, to minimize impurities, gentisic acid may be excluded from the incorporation reaction.

3. HPLC Verification

In FIG. 1A, HPLC shows an incorporation reaction with acetate and gentisic acid (peak at 10.2 min always appears): 20 min reactions at 90° C. In FIGS. 1B-1C, HPLC shows reactions with gentisic acid and ascorbate (peak at 10.2 min appears sometimes): 20 min reactions at 90° C. In FIG. 1D, HPLC shows reaction with just ascorbate (peak at ~10.2 min never appears): 20 min reactions at 90° C.

4. Positive Impact of Gentisic Acid in the Formulation Composition

It was found that inclusion of gentisic acid in the Formulation Composition at the time of or following termination of the reaction incorporating Lu-177 with EuK-Sub-kf-iodo-y-DOTAGA favorably impacted radiochemical purity of the $^{177}$Lu-PSMA-I&T or lutetium ($^{177}$Lu) zadavotide guraxetan. That is, inclusion of gentisic acid in the Formulation Composition showed a reduced drop in radiochemical purity over time. Thus, over the 5 or 6 day evaluation period, in Experiment 3c where gentisic acid was not present in the Formulation Composition, radiochemical purity dropped 10.2%, whereas in Experiment 3d where gentisic acid was present in the Formulation Composition, radiochemical purity dropped 7.6%.

Example 2

Figure 2:
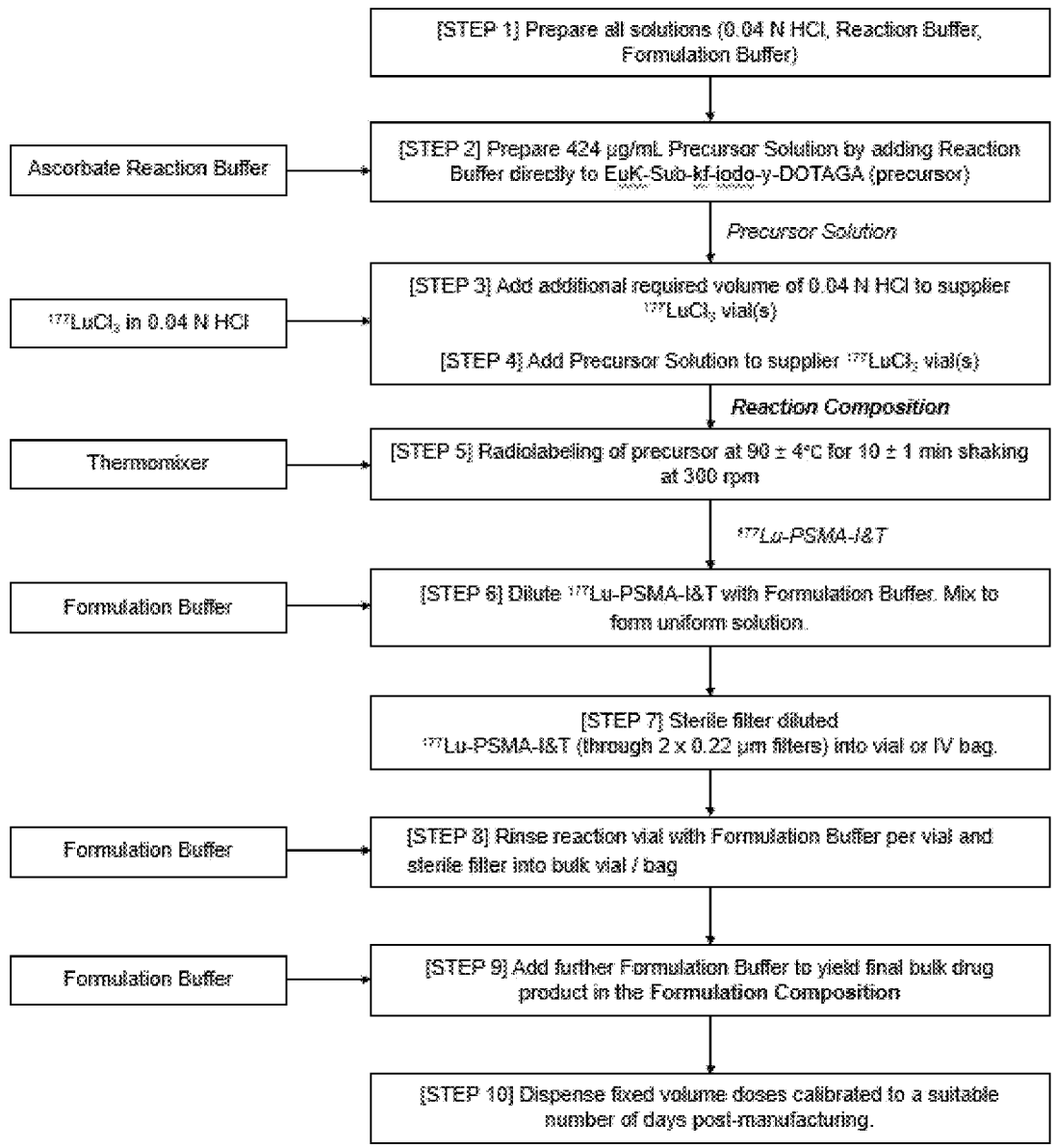
FIG. 2 shows schematically the general synthesis and formulation of $^{177}$Lu-PSMA I&T in Example 2 which follows.

The following is a preferred preparation process as also generally depicted schematically in FIG. 2.
 (1) Prepare all solutions
   a. Reaction Buffer prepared by combining sodium L-ascorbate and ascorbic acid to yield approximately 162 mg/mL Ascorbate (pH 5.5-6).
   b. Formulation Buffer prepared by combining sodium L-ascorbate and gentisic acid to yield approximately 66 mg/mL Ascorbate with approximately 28 mg/mL Gentisic acid (pH 6-7).
   c. 0.04 N HCl
 (2) Using Reaction Buffer, dissolve 250 ug of precursor (i.e. racemic EuK-Sub-kf-iodo-y-DOTAGA or R-isomer of EuK-Sub-kf-iodo-y-DOTAGA (compound of formula 1A)) to approximately 424 µg/mL (Precursor Solution).
 (3) Add additional 0.04N HCl to the lutetium-177 vial (Reaction vial) in order to achieve a radioactive concentration of 7.8 GBq/mL).
 (4) Add sufficient quantity of the Precursor Solution to the lutetium-177 vial (Reaction vial) containing no-carrier added lutetium-177 in 0.4 N HCl
 (5) Heat vial containing the Reaction Composition in an aluminum block with heating at 90+/−4° C. and shaking at 300 rpm for 10+/−1 min.
 (6) Add Formulation Buffer into vial (Formulation vial) and mix the Reaction vial to ensure homogeneity of the contents.
 (7) Sterile filter diluted $^{177}$Lu-PSMA-I&T (through 2×0.22 µm filters) into a vial or IV bag.
 (8) Rinse Reaction Vial with a sufficient quantity of and sterile filter rinse (through 2×0.22 µm filters) into a vial or IV bag with the diluted 177Lu-PSMA-I&T.
 (9) Add further Formulation Buffer to yield final bulk drug product in the Formulation Composition.
 (10) Dispense fixed volume doses calibrated to a suitable number of days post-manufacturing.

The above process also can be utilized to prepare $^{177}$Lu-PSMA I&T that is substantially optically enriched with or is an enantiomerically pure mixture of the S-isomer of $^{177}$Lu-PSMA I&T (compound of formula 2B above) by use of the S-isomer of EuK-Sub-kf-iodo-y-DOTAGA (compound of formula 1B)).

Example 3: Treatment Protocol

A human male patient is selected for treatment after being diagnosed with metastatic castration-resistant prostate cancer (such as manifested by progression of the disease despite surgical or chemical castration) who have progressed following treatment first line androgen receptor-axis-targeted (ARAT) therapies.

Lutetium ($^{177}$Lu) zadavotide guraxetan in a sterile aqueous solution is administered by intravenous injection. The dosing regimen may include four infusions of 6.8 GBq+/−10% each, administered 8 weeks apart.

INCORPORATION BY REFERENCE

The entire contents of all patents, published patent applications and other disclosures cited herein are hereby expressly incorporated herein in their entireties by reference.

What is claimed is:

1. A method for preparing a complex of lutetium-177 and EuK-Sub-kf-iodo-y-DOTAGA, comprising:
   a) admixing in the absence of a gentisate compound:
      1) lutetium-177;
      2) EuK-Sub-kf-iodo-y-DOTAGA; and
      3) one or more stabilizer compounds; and
   b) heating the admixed 1) lutetium-177, 2) EuK-Sub-kf-iodo-y-DOTAGA, and 3) one or more stabilizer compounds in the absence of a gentisate compound;
   wherein a complex of lutetium-177 and EuK-Sub-kf-iodo-y-DOTAGA is formed without the addition of a gentisate compound.

2. The method of claim 1 wherein the one or more stabilizer compounds comprise one or more ascorbate compounds.

3. The method of wherein the complex of lutetium-177 and EuK-Sub-kf-iodo-y-DOTAGA is:
   1) free of unchelated lutetium-177 in an amount of 1 weight % or less; and/or
   2) free of radiochemical impurities in an amount of 3 weight % or less; and/or
   3) free of chemical impurities in an amount of 5 weight % or less,
   all weight % based on total weight of the complex of lutetium-177 and EuK-Sub-kf-iodo-y-DOTAGA, and
   where complex is maintained at 30° C. or less and such purity levels are exhibited for 3 days or more following formation of the complex.

4. The method of claim 1 wherein the complex of lutetium-177 and EuK-Sub-kf-iodo-y-DOTAGA is formed free of an impurity having a retention time of approximately 9 to 12 minutes by high-performance liquid chromatography.

5. The method of claim 1 wherein the admixture is heated at a temperature not exceeding 94° C.

6. The method of claim 1 wherein incorporation of lutetium-177 and EuK-Sub-kf-iodo-y-DOTAGA is greater than 98 mole percent.

7. The method of claim 1 wherein the complex of lutetium-177 and EuK-Sub-kf-iodo-y-DOTAGA corresponds to the following structure:

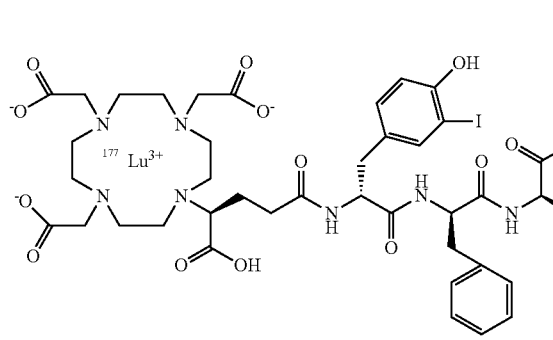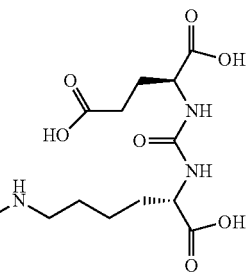

8. The method of claim 1 wherein the complex of lutetium-177 and EuK-Sub-kf-iodo-y-DOTAGA is formed in the complete absence of a gentisate compound.

9. The method of claim 1 consisting essentially of:
 a) admixing in the absence of a gentisate compound:
  1) lutetium-177;
  2) EuK-Sub-kf-iodo-y-DOTAGA; and
  3) one or more stabilizer compounds; and
 b) heating the admixed 1) lutetium-177, 2) EuK-Sub-kf-iodo-y-DOTAGA, and 3) one or more stabilizer compounds in the absence of a gentisate compound;
 wherein a complex of lutetium-177 and EuK-Sub-kf-iodo-y-DOTAGA is formed without the addition of a gentisate compound.

10. The method of claim 9 wherein the complex of lutetium-177 and EuK-Sub-kf-iodo-y-DOTAGA is formed in the complete absence of a gentisate compound.

11. The method of claim 1 consisting of:
 a) admixing in the absence of a gentisate compound:
  1) lutetium-177;
  2) EuK-Sub-kf-iodo-y-DOTAGA; and
  3) one or more stabilizer compounds; and
 b) heating the admixed 1) lutetium-177, 2) EuK-Sub-kf-iodo-y-DOTAGA, and 3) one or more stabilizer compounds in the absence of a gentisate compound;
 wherein a complex of lutetium-177 and EuK-Sub-kf-iodo-y-DOTAGA is formed without the addition of a gentisate compound.

* * * * *

(12) EX PARTE REEXAMINATION CERTIFICATE (12254th)
United States Patent
McCann

(10) Number: US 11,129,912 C1
(45) Certificate Issued: Mar. 27, 2023

(54) RADIOPHARMACEUTICAL AND METHODS

(71) Applicant: Point Biopharma, Inc., Toronto (CA)

(72) Inventor: Joe McCann, Toronto (CA)

(73) Assignee: POINT BIOPHARMA, INC., Toronto (CA)

Reexamination Request:
No. 90/015,012, Apr. 21, 2022

Reexamination Certificate for:
Patent No.: 11,129,912
Issued: Sep. 28, 2021
Appl. No.: 17/162,856
Filed: Jan. 29, 2021

Related U.S. Application Data

(60) Provisional application No. 63/051,335, filed on Jul. 13, 2020.

(51) Int. Cl.
*A61K 51/04* (2006.01)
*A61P 35/00* (2006.01)
*C07B 59/00* (2006.01)

(52) U.S. Cl.
CPC .......... *A61K 51/0482* (2013.01); *A61P 35/00* (2018.01); *C07B 59/002* (2013.01)

(58) Field of Classification Search
None
See application file for complete search history.

(56) References Cited

To view the complete listing of prior art documents cited during the proceeding for Reexamination Control Number 90/015,012, please refer to the USPTO's Patent Electronic System.

*Primary Examiner* — Dwayne C. Jones

(57) ABSTRACT

The radiopharmaceutical $^{177}$Lu-PSMA I&T is provided, including in high purities with extended shelf life. Further provided are methods of synthesis of $^{177}$Lu-PSMA I&T and pharmaceutical compositions and methods of treatment that comprise $^{177}$Lu-PSMA I&T.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 17-20:

[In such aspect, generally preferred is EuK-Sub-kf-iodo-y-DOTAGA that is substantially optically enriched with the S isomer of formula 1B, or is an enantiomerically pure mixture of the S isomer of formula 11.]

Column 3, lines 17-20:

*In such aspect, generally preferred is EuK-Sub-kf-iodo-y-DOTAGA that is substantially optically enriched with the S isomer of formula 1B, or is an enantiomerically pure mixture of the S isomer of formula 1B.*

Column 3, lines 43-49:

[In this aspect, generally preferred is $^{177}$Lu-PSMA I&T that is substantially optically enriched with the R isomer of formula 2A, or is an enantiomerically pure mixture of the R isomer of formula 2A In another aspect, the S isomer of $^{177}$LuPSMA I&T is provided, including for use in the present pharmaceutical compositions and methods. That S isomer may be represented by the following structure 213.]

Column 3, lines 43-49:

*In this aspect, generally preferred is $^{177}$Lu-PSMA I&T that is substantially optically enriched with the R isomer of formula 2A, or is an enantiomerically pure mixture of the R isomer of formula 2A. In another aspect, the S isomer of $^{177}$LuPSMA I&T is provided, including for use in the present pharmaceutical compositions and methods. That S isomer may be represented by the following structure 2B.*

AS A RESULT OF REEXAMINATION, IT HAS BEEN DETERMINED THAT:

Claims 2, 5 and 7-11 are cancelled.

Claims 1 and 3 are determined to be patentable as amended.

Claims 4 and 6, dependent on an amended claim, are determined to be patentable.

1. A method for preparing a complex of lutetium-177 and EuK-Sub-kf-iodo-y-DOTAGA, comprising:
   a) admixing in the *complete* absence of a gentisate compound:
      1) lutetium-177;
      2) EuK-Sub-kf-iodo-y-DOTAGA; and
      3) one or more [stabilizer] *ascorbate* compounds *in an amount between 55 mg/mL to 75 mg/mL*; and
   b) heating the admixed 1) lutetium-177, 2) EuK-Sub-kf-iodo-y-DOTAGA, and 3) one or more [stabilizer] *ascorbate* compounds in the absence of a gentisate compound *and at a temperature not exceeding 94° C.*;
   wherein a complex of lutetium-177 and EuK-Sub-kf-iodo-y-DOTAGA is formed without the addition of a gentisate compound; *and*
   c) *cooling the complex formed in step b) and admixing the complex with one or more ascorbate compounds and one or more gentisate compounds to provide a radiopharmaceutical composition that maintains radiochemical purity of at least 95% for 3 days wherein the amount of one or more ascorbate compounds is between 10 mg/mL to 100 mg/mL and the amount of one or more gentisate compounds is between 5 mg/mL to 100 mg/mL.*

3. The method of claim 1 wherein the complex of lutetium-177 and EuK-Sub-kf-iodo-y-DOTAGA is:
   1) free of unchelated lutetium-177 in an amount of 1 weight % or less; and/or
   2) free of radiochemical impurities in an amount of 3 weight % or less; and/or
   3) free of chemical impurities in an amount of 5 weight % or less, all weight % based on total weight of the complex of lutetium-177 and EuK-Sub-kf-iodo-y-DOTAGA, and
   where *the* complex is maintained at 30° C. or less and such purity levels are exhibited for 3 days or more following formation of the complex.

\* \* \* \* \*